US012728190B2

(12) United States Patent
Patel et al.

(10) Patent No.: US 12,728,190 B2
(45) Date of Patent: Sep. 8, 2026

(54) CSF DIAGNOSTICS PLATFORM

(71) Applicant: EnClear Therapies, Inc., Newburyport, MA (US)

(72) Inventors: Rajan Patel, Newburyport, MA (US); Gianna N. Riccardi, South Berwick, ME (US); Kevin Kalish, Newburyport, MA (US); Marcie Glicksman, Salem, MA (US)

(73) Assignee: EnClear Therapies, Inc., Newburyport, MA (US)

( * ) Notice: Subject to any disclaimer, the term of this patent is extended or adjusted under 35 U.S.C. 154(b) by 770 days.

(21) Appl. No.: 17/868,484

(22) Filed: Jul. 19, 2022

(65) Prior Publication Data

US 2022/0355015 A1 Nov. 10, 2022

Related U.S. Application Data

(63) Continuation-in-part of application No. 17/848,211, filed on Jun. 23, 2022, which is a continuation-in-part
(Continued)

(51) Int. Cl.

| | |
|---|---|
| ***A61M 1/36*** | (2006.01) |
| ***A61M 1/16*** | (2006.01) |
| ***A61M 27/00*** | (2006.01) |

(52) U.S. Cl.

CPC ............ *A61M 1/3687* (2013.01); *A61M 1/16* (2013.01); *A61M 1/1601* (2014.02);
(Continued)

(58) Field of Classification Search

CPC ........ A61M 27/006; A61M 2027/0004; A61M 2202/0464; A61M 1/14; A61M 1/34; A61M 1/36

See application file for complete search history.

(56) References Cited

U.S. PATENT DOCUMENTS

| | | | |
|---|---|---|---|
| 3,929,992 | A | 12/1975 | Sehgal et al. |
| 4,316,885 | A | 2/1982 | Rakhit |

(Continued)

FOREIGN PATENT DOCUMENTS

| | | | |
|---|---|---|---|
| CN | 203604173 | U | 5/2014 |
| CN | 106362226 | A | 2/2017 |

(Continued)

OTHER PUBLICATIONS

Martin, L., et al., "Post-translational modifications of tau protein: implications for Alzheimer's disease," Neurochemistry International, vol. 58, Issue 4, pp. 458-471.

(Continued)

*Primary Examiner* — Leslie R Deak

(74) *Attorney, Agent, or Firm* — Nutter McClennen & Fish LLP

(57) ABSTRACT

The present disclosure generally relates to a system for flowing a fluid, e.g., CSF, from a body of a patient for sampling and analysis. In some embodiments, the system can include a diagnostic module having one or more conduits for flowing fluid therethrough. The flow of the fluid through the valves can be regulated using a control board that changes an orientation of valves disposed in the conduits between a dead-end orientation and a flow-through orientation to sample and/or analyze the fluid from the system. In some embodiments, the fluid can be recirculated into the system through one or more of the valves, with sampling and recirculating occurring substantially simultaneously.

39 Claims, 12 Drawing Sheets

Related U.S. Application Data of application No. 17/669,883, filed on Feb. 11, 2022, now Pat. No. 12,350,416, and a continuation-in-part of application No. 17/495,682, filed on Oct. 6, 2021, and a continuation-in-part of application No. 17/489,620, filed on Sep. 29, 2021, now Pat. No. 12,337,140, said application No. 17/669,883 is a continuation of application No. 17/062,440, filed on Oct. 2, 2020, now Pat. No. 11,278,657, which is a continuation of application No. PCT/US2020/027683, filed on Apr. 10, 2020.

(60) Provisional application No. 63/223,248, filed on Jul. 19, 2021, provisional application No. 63/214,239, filed on Jun. 23, 2021, provisional application No. 63/117,975, filed on Nov. 24, 2020, provisional application No. 63/088,401, filed on Oct. 6, 2020, provisional application No. 63/084,996, filed on Sep. 29, 2020, provisional application No. 62/960,861, filed on Jan. 14, 2020, provisional application No. 62/832,486, filed on Apr. 11, 2019.

(52) U.S. Cl.
CPC ......... *A61M 27/006* (2013.01); *A61M 1/3655* (2013.01); *A61M 1/3659* (2014.02); *A61M 2027/004* (2013.01); *A61M 2202/0464* (2013.01); *A61M 2205/103* (2013.01); *A61M 2205/12* (2013.01); *A61M 2205/3334* (2013.01); *A61M 2205/3344* (2013.01); *A61M 2205/3379* (2013.01); *A61M 2210/1003* (2013.01); *A61M 2210/1039* (2013.01)

(56) References Cited

U.S. PATENT DOCUMENTS 4,366,241 A 12/1982 Tom et al.
4,376,110 A 3/1983 David et al.
4,382,445 A 5/1983 Sommers
4,517,288 A 5/1985 Giegel et al.
4,650,803 A 3/1987 Stella et al.
4,655,745 A 4/1987 Corbett
4,830,849 A 5/1989 Osterholm
4,837,168 A 6/1989 de Jaeger et al.
4,950,232 A 8/1990 Ruzicka et al.
5,023,263 A 6/1991 Von Burg
5,023,264 A 6/1991 Caufield et al.
5,100,883 A 3/1992 Schiehser
5,118,677 A 6/1992 Caufield
5,118,678 A 6/1992 Kao et al.
5,120,842 A 6/1992 Failli et al.
5,130,307 A 7/1992 Failli et al.
5,162,333 A 11/1992 Failli et al.
5,177,203 A 1/1993 Failli et al.
5,221,670 A 6/1993 Caufield
5,233,036 A 8/1993 Hughes
5,256,790 A 10/1993 Nelson
5,258,389 A 11/1993 Goulet et al.
5,260,300 A 11/1993 Hu
5,262,423 A 11/1993 Kao
5,302,584 A 4/1994 Kao et al.
5,362,718 A 11/1994 Skotnicki et al.
5,373,014 A 12/1994 Failli et al.
5,378,836 A 1/1995 Kao et al.
5,385,908 A 1/1995 Nelson et al.
5,385,909 A 1/1995 Nelson et al.
5,385,910 A 1/1995 Ocain et al.
5,389,639 A 2/1995 Failli et al.
5,391,730 A 2/1995 Skotnicki et al.
5,405,316 A 4/1995 Magram
5,411,967 A 5/1995 Kao et al.
5,434,260 A 7/1995 Skotnicki et al.
5,463,048 A 10/1995 Skotnicki et al.
5,480,988 A 1/1996 Failli et al.
5,480,989 A 1/1996 Kao et al.
5,489,680 A 2/1996 Failli et al.
5,491,231 A 2/1996 Nelson et al.
5,504,091 A 4/1996 Molnar-Kimber et al.
5,531,673 A 7/1996 Helenowski
5,563,145 A 10/1996 Failli et al.
5,665,772 A 9/1997 Cottens et al.
5,780,462 A 7/1998 Lee et al.
5,957,912 A 9/1999 Heitzmann
6,193,691 B1 2/2001 Beardsley
6,210,346 B1 4/2001 Hall et al.
6,273,913 B1 8/2001 Wright et al.
6,277,983 B1 8/2001 Shaw et al.
6,358,969 B1 3/2002 Shelley et al.
6,471,960 B1 10/2002 Anderson
6,585,764 B2 7/2003 Wright et al.
6,599,275 B1 7/2003 Fischer, Jr.
6,670,168 B1 12/2003 Katz et al.
6,689,085 B1 2/2004 Rubenstein et al.
6,696,488 B2 2/2004 Wolfe et al.
6,808,536 B2 10/2004 Wright et al.
6,916,310 B2 7/2005 Sommerich
7,025,739 B2 4/2006 Saul
7,037,288 B2 5/2006 Rosenberg et al.
7,331,940 B2 2/2008 Sommerich
7,662,140 B2 2/2010 Heruth et al.
7,717,871 B2 5/2010 Odland
7,763,142 B2 7/2010 Watson
7,887,503 B2 2/2011 Geiger
8,088,091 B2 1/2012 Thomas et al.
8,137,334 B2 3/2012 Heruth et al.
8,206,334 B2 6/2012 Kralick et al.
8,216,173 B2 7/2012 Dacey, Jr. et al.
8,292,856 B2 10/2012 Bertrand et al.
8,435,204 B2 5/2013 Lad et al.
9,097,723 B2 8/2015 Fathollahi et al.
9,138,537 B2 9/2015 Miesel
9,220,424 B2 12/2015 Wilson et al.
9,421,348 B2 8/2016 Lenihan et al.
9,603,792 B2 3/2017 John
9,629,987 B2 4/2017 Anand et al.
9,687,670 B2 6/2017 Dacey, Jr. et al.
9,744,338 B2 8/2017 East et al.
9,770,180 B2 9/2017 Radojicic
9,895,518 B2 2/2018 Lad et al.
9,919,138 B2 3/2018 Lenihan et al.
10,258,781 B2 4/2019 Choi et al.
10,272,188 B1 4/2019 Geiger et al.
10,441,770 B2 10/2019 Singh et al.
10,549,035 B2 2/2020 Hayek
10,695,484 B1 6/2020 Radojicic
11,278,657 B2 3/2022 DePasqua et al.
11,534,592 B2 12/2022 Singh et al.
2002/0004580 A1 1/2002 Fueyo et al.
2002/0025521 A1 2/2002 Lu et al.
2003/0060436 A1 3/2003 Schneider
2003/0135148 A1 7/2003 Dextradeur et al.
2004/0068241 A1 4/2004 Fischer
2004/0110250 A1 6/2004 Wischik et al.
2004/0138153 A1 7/2004 Ramesh et al.
2004/0185042 A1 9/2004 Scheiflinger et al.
2004/0220510 A1 11/2004 Koullick et al.
2004/0236309 A1 11/2004 Yang
2006/0025726 A1 2/2006 Fischer et al.
2006/0074388 A1 4/2006 Dextradeur et al.
2006/0079740 A1 4/2006 Silver et al.
2006/0264897 A1 11/2006 Lobl et al.
2007/0167867 A1 7/2007 Wolf
2007/0173787 A1 7/2007 Huang et al.
2007/0243179 A1 10/2007 Elia
2008/0082036 A1 4/2008 Trescony et al.
2008/0242590 A1 10/2008 Andersson et al.
2009/0131857 A1 5/2009 Geiger
2010/0022896 A1 1/2010 Yadav et al.
2010/0030196 A1 2/2010 Hildebrand et al.
2010/0234792 A1 9/2010 Dacey, Jr. et al.
2011/0033463 A1 2/2011 Thakker et al.

(56) References Cited

U.S. PATENT DOCUMENTS

2012/0238835 A1 9/2012 Hyde et al.
2012/0238936 A1 9/2012 Hyde et al.
2013/0273203 A1 10/2013 Oestergaard et al.
2014/0018257 A1 1/2014 Suga et al.
2014/0206102 A1 7/2014 Petrucelli et al.
2014/0303455 A1 10/2014 Shachar et al.
2014/0377319 A1 12/2014 Leuthardt et al.
2015/0005800 A1 1/2015 Anile
2015/0201882 A1 7/2015 Swoboda et al.
2015/0374898 A1 12/2015 Fujieda et al.
2016/0002627 A1 1/2016 Bennett et al.
2016/0025747 A1 1/2016 Ranum et al.
2016/0051801 A1 2/2016 Vase
2016/0089521 A1 3/2016 Dragoon et al.
2016/0183819 A1 6/2016 Burnett et al.
2016/0361365 A1 12/2016 Lee et al.
2017/0059586 A1 3/2017 Petrucelli et al.
2017/0095649 A1 4/2017 Vase et al.
2017/0137492 A1 5/2017 Looby
2017/0157038 A1 6/2017 Peyman
2017/0157374 A1 6/2017 Hedstrom et al.
2017/0203084 A1 7/2017 Lad et al.
2017/0313687 A1 11/2017 Hendrickson et al.
2018/0028746 A1 2/2018 Abrams et al.
2018/0185058 A1 7/2018 Anand et al.
2018/0371010 A1 12/2018 Vassylyev et al.
2019/0009014 A1 1/2019 Chen et al.
2019/0048371 A1 2/2019 Basheer et al.
2019/0083303 A1 3/2019 Khanna
2019/0085336 A1 3/2019 Zhu et al.
2019/0089521 A1 3/2019 Coulthard et al.
2019/0317099 A1 10/2019 Halbert et al.
2020/0001059 A1 1/2020 Campbell et al.
2020/0046952 A1 2/2020 Vase
2020/0046954 A1 2/2020 Lad et al.
2020/0118676 A1 4/2020 Spohn et al.
2020/0330497 A1 10/2020 Marcotulli et al.
2021/0023293 A1 1/2021 DePasqua et al.
2021/0033620 A1 2/2021 Porter et al.
2021/0077016 A1 3/2021 Bodner
2021/0145944 A1 5/2021 Navia et al.
2021/0154276 A1 5/2021 Navia et al.
2021/0162173 A1 6/2021 Singh et al.
2022/0096743 A1 3/2022 Riccardi et al.
2022/0096744 A1 3/2022 Riccardi et al.
2022/0096745 A1 3/2022 Riccardi et al.
2022/0105322 A1 4/2022 Riccardi et al.
2022/0134076 A1 5/2022 Bodner
2022/0160947 A1 5/2022 DePasqua et al.
2022/0257854 A1 8/2022 Bodner et al.
2022/0313890 A1 10/2022 Riccardi et al.
2022/0370716 A1 11/2022 Martin et al.
2022/0379010 A1 12/2022 Martin et al.
2022/0401645 A1 12/2022 Morse et al.
2023/0001165 A1 1/2023 Bourouiba et al.
2023/0056486 A1 2/2023 Navia et al.

FOREIGN PATENT DOCUMENTS

EP 1481697 B1 2/2007
EP 1731182 B1 9/2012
EP 3294398 A1 3/2018
EP 3833251 A1 6/2021
EP 4030988 A1 7/2022
JP 2002/136295 A 5/2002
WO 98/02441 A2 1/1998
WO 99/13886 A1 3/1999
WO 99/15530 A1 4/1999
WO 2000/056335 A1 9/2000
WO 01/14387 A1 3/2001
WO 2001/039819 A2 6/2001
WO 2003015710 A2 2/2003
WO 03/057218 A1 7/2003
WO 2003/015710 A3 2/2004
WO 2004/058337 A1 7/2004
WO 2004/091444 A2 10/2004
WO 2008/105959 A2 9/2008
WO 2008140546 A2 11/2008
WO 2010123558 A1 10/2010
WO 2011114260 A1 9/2011
WO 2014/159247 A1 10/2014
WO 2014/159757 A2 10/2014
WO 2015/049588 A2 4/2015
WO 2014/124365 A3 10/2015
WO 2016183123 A1 11/2016
WO 2017096228 A1 6/2017
WO 2018005621 A1 1/2018
WO 2018/160993 A1 9/2018
WO 2019/028006 A1 2/2019
WO 2019/100074 A1 5/2019
WO 2020/023417 A1 1/2020
WO 2020/023418 A1 1/2020
WO 2020/033773 A1 2/2020
WO 2020064875 A1 4/2020
WO 2020/0149993 A1 7/2020
WO 2020/210634 A1 10/2020
WO 2021/055100 A1 3/2021
WO 2022/076598 A1 4/2022
WO 2022/173620 A1 8/2022
WO 2022/246042 A1 11/2022

OTHER PUBLICATIONS

Marx, S., et al., "Bench to Bedside: The Development of Rapamycin and Its Application to Stent Restenosis", Journal of the American Heart Association 104, 2001, pp. 852-855.
May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.
Mckee, A., et al., "The Neuropathology of Chronic Traumatic Encephalopathy," Brain Pathology 253), 2015, pp. 350-364.
Mcrae et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, pp. 7196-7206.
Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.
Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.
Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.
Neumann, M., et al., "Ubiquitinated TDP-43 in frontotemporal lobar degeneration and amyotrophic lateral sclerosis," Science, vol. 314, 2006, pp. 130-133.
Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.
Ozcelik, A., et al., "Acoustic tweezers for the life sciences," Nature Methods vol. 15, 2018, pp. 1021-1028.
Paraskevas, G., et al., "The emerging TDP-43 proteinpathy" Neuroimmunol Neuroinflammation 5:17 (Year 2018).
Pardridge, W., et al., "CSF, blood-brain barrier, and brain drug delivery," Expert Opinion on Drug Delivery, vol. 13, 2016, pp. 1-13.
Patel, A., et al., "Identification and enumeration of circulating tumor cells in the cerebrospinal fluid of breast cancer patents with central nervous system metastases," Oncotarget, vol. 2, No. 10, 2011, pp. 752-760.
Paulson, H., et al., "Genetics of Dementia," Seminars in Neurology, vol. 31, pp. 449-360.
Phukan, J., et al., "Cognitive impairment in amyotrophic lateral sclerosis," The Lancet Neurology, vol. 6, Issue 11, pp. 994-1003.
Poreba, M., et al., "Current Strategies for Probing Substrate Specificity of Proteases," Current Medicinal Chemistry, vol. 17, Issue 33, 2010, pp. 3968-3995.

(56) References Cited

OTHER PUBLICATIONS

Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.
Reinhard, M., et al., "Blood-Brain Barrier Disruption by Low-Frequency Ultrasound," Stroke, vol. 37, 2006, pp. 1546-1548.
Renton, A., et al., "A Hexanucleotide Repeat Expansion in C9ORF72 Is the Cause of Chromosome 9p21-Linked ALS-FTD," Neuron, vol. 27, Issue 2, pp. 257-268.
Saido, T., et al., "Proteolytic Degradation of Amyloid 13-Protein" Cold Spring Harbor Perspectives in Medicine, vol. 2, No. 6, Jun. 1, 2012, pp. a006379-a006379.
Sonabend, A., et al., "Overcoming the Blood-Brain Barrier with an Implantable Ultrasound Device," Clinical Cancer Research, vol. 25, Issue 13, 2019, pp. 3750-3752.
Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Spencer, B., et al., "Lentivirus Mediated Delivery of Neurosin Promotes Clearance of Wild-type a-Synuclein and Reduces the Pathology in an a-Synuclein Model of LBD", Molecular Therapy, vol. 21, No. 1, Jan. 1, 2013, pp. 31-41.
Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
Takalo, M., et al., "Protein aggregation and degradation mechanisms in neurodegenerative diseases," American Journal of Neurodegenerative Disease, 2013; 2(1), pp. 1-14.
Tanji, K., et al., "Proteinase K-resistant a-synuclein is deposited in presynapses in human Lewy body disease and A53T a-synuclein transgenic mice," Acta Neuropathologica, Springer, Berlin, DE, vol. 120, No. 2, Mar. 26, 2010, pp. 145-154.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency, Ultrasound," PLOS ONE vol. 3, Issue 10, 2008, e3511, 11 pages.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N?terminally cleaved tau containing four microtubule?binding repeats," Journal of Neurochemistry, vol. 105, 2008, pp. 2343-2352.
Written Opinion of the International Preliminary Examining Authority for International Application No. PCT/US2019/042879, mailed Feb. 25, 2021 (6 pages).
Written Opinion of the International Preliminary Examining Authority for International Application No. PCT/US2019/042880, mailed Sep. 11, 2020 (8 pages).
Wszolek, Z., et al., "Frontotemporal dementia and parkinsonism linked to chromosome 17 (FTDP-17)" Orphanet Journal of Rare Diseases, 2006, 1:30, pp. 1-9.
Xie, L., et al., "Sleep Drives Metabolite Clearance from the Adult Brain," Science vol. 342, Issue 6156, 2013, pp. 373-377.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.
Abbott, N., et al., "The role of brain barriers in fluid movement in the CNS: is there a 'glymphatic' system?" Acta Neuropathologica vol. 135, 2018, pp. 387-407.
Allen, J., et al., "Abstract 3483: Modeling circulating tumor cells in the peripheral blood and CSF of breast cancer patients," Cancer Research vol. 73, Issue 8, 2013, abstract only.
Allen, J., et al., "Abstract 5565: Circulating tumor cells in the peripheral blood and cerebrospinal fluid of patients with central nervous system metastases," Cancer Research vol. 72, Issue 8, 2012, abstract only.
Andersen, P., et al., "Clinical genetics of amyotrophic lateral sclerosis: what do we really know?" Nature Reviews Neurology, vol. 7, 2011, pp. 603-615.
Arai, T., et al., "Phosphorylated and cleaved TDP?43 in ALS, FTLD and other neurodegenerative disorders and in cellular models of TDP?43 proteinopathy," Neuropathology, vol. 30, 2010, pp. 170-181.
Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.
Arriagada, P., et al., "Neurofibrillary tangles but not senile plaques parallel duration and severity of Alzheimer's disease," Neurology 42, 1992, pp. 631-639.
Asai, D., et al., "Chapter 3 Making Monoclonal Antibodies," Methods in Cell Biology, vol. 37, 1993, pp. 57-74.
Bioline "Proteinase K" accessed from bioline.com on Jun. 22, 2021 (Year: 2013).
Brat, D., et al., "Tau?associated neuropathology in ganglion cell tumours increases with patient age but appears unrelated to ApoE genotype," Neuropathy and Applied Neurobiology, vol. 27, Issue 3, 2001, pp. 197-205.
Buee, L., et al., "Tau protein isoforms, phosphorylation and role in neurodegenerative disorders," Brain Research Reviews, vol. 33, Issue 1, 2000, pp. 95-130.
Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.
Coatti, G., et al., "Pericytes Extended Survival of ALS SOD1 Mice and Induce the Expression of Antioxidant Enzymes in the Murine Model and in IPSCs Dervised Neuronal Cells from an ALS Patient," Stem Cell Reviews and Reports (2017) 13: 686-698.
De Souza, P., et al., "A biotechnology perspective of fungal proteases," Brazilian Journal of Microbiology, vol. 46, 2, 2015, pp. 337-346.
Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.
Diamond, S., "Methods for mapping protease specificity," Current Opinion in Chemical Biology, vol. 11, Issue 1, 2007, pp. 46-51.
Evidente, V., et al., "Post-encephalitic parkinsonism," Journal of Neurology, Neurosurgery & Psychiatry, vol. 63, Issue 1, 1998, pp. 5.
Extended European Search Report for European Application No. 19839881.0 dated Jun. 21, 2022, 9 pages.
Extended European Search Report for European Application No. 19840444.4 dated Jun. 28, 2022, 7 pages.
Finsterer, J., et al., "Liquorpheresis (CSF filtration) in familial amyotrophic lateral sclerosis," Spinal Cord, vol. 39, 1999, pp. 592-593.
Giannakopoulos, P., et al., Tangle and neuron numbers, but not amyloid load, predict cognitive status in Alzheimer's disease, Neurology, vol. 60, 2003, pp. 1495-1500.
Giordana, M., et al., "Dementia and cognitive impairment in amyotrophic lateral sclerosis: a review," Neurological Sciences, vol. 32, 2011, pp. 9-16.
Gomez-Isla, T., et al., Neuronal loss correlates with but exceeds neurofibrillary tangles in Alzheimer's disease, Annals of Neurology, vol. 41, 1997, pp. 17-24.
Grad, L., et al., "Prion-like activity of Cu/Zn superoxide dismutase: implications for amyotrophic lateral sclerosis," 8:1, 2014, pp. 33-41.
Graff-Radford, N., et al., "Frontotemporal dementia," Seminars in Neurology vol. 27, 2007, pp. 48-57.
Hasegawa, M., et al., "Molecular Dissection of TDP-43 Proteinopathies," Journal of Molecular Neuroscience, vol. 45, 2011, pp. 480-485.
Hasegawa, M., et al., "Phosphorylated TDP-43 in frontotemporal lobar degeneration and amyotrophic lateral sclerosis," Annals of Neurology, vol. 62, Issue 1, 2008, pp. 60-70.

(56) References Cited

OTHER PUBLICATIONS

Hersh, D., et al., "MR-guided transcranial focused ultrasound safely enhances interstitial dispersion of large polymeric nanoparticles in the living brain," PLOS ONE 13(2): e0192240, 2018, 19 pages.
Indivero, V., "Technique filters cancer where chemo can't reach: A new therapy may help cancer patients with malignant ce4lls near the spinal cord and in the brain," dated Jul. 30, 2013. Retrieved from the internet under https://news.psu.edu/story/282970/2013/07/30/research/technique-filters-cancer-where-chemo-cant-reach, 4 pages.
International Preliminary Report on Patentability for International Application No. PCT/US2019/042880, mailed Jan. 12, 2021 (8 pages).
International Preliminary Report on Patentability for International Application No. PCT/US2020/027683, mailed Oct. 21, 2021 (11 pages).
International Search Report and Written Opinion for International Application No. PCT/US2019/042879, mailed Oct. 8, 2019 (14 pages).
International Search Report and Written Opinion for International Application No. PCT/US2019/042880, mailed Oct. 16, 2019 (10 pages).
International Search Report and Written Opinion for International Application No. PCT/US2020/027683, mailed Aug. 6, 2020 (19 pages).
International Search Report and Written Opinion for International Application No. PCT/US2021/013458, mailed Jun. 9, 2021 (20 pages).
International Search Report and Written Opinion for International Application No. PCT/US2021/052735, mailed Feb. 11, 2022, 28 pages.
International Search Report and Written Opinion for International Application No. PCT/US2021/053829 mailed Jan. 13, 2022. 19 pages.
International Searching Authority, International Search Report for International Application No. PCT/US2022/037609, dated Oct. 26, 2022, together with the Written Opinion of the International Searching Authority, 8 pages.
International Searching Authority, International Search Report for International Application No. PCT/US22/34706, dated Oct. 18, 2022, together with the Written Opinion of the International Searching Authority, 8 pages.
Jessen, N., et al., "The Glymphatic System—A Beginner's Guide," Neurochemical Research, 2015, 40(2), pp. 2583-2599.
Kaufman, S., et al., "Prion-Like Propagatio of Protein Aggregation and Related Therapeutic Strategies," Neurotherapeutics, 10, 2013, pp. 371-382.
Kim Kwang Soo, et al., "Proteolytic Cleavage of Extracellular a-Synuclein by Plasmin: Implications for Parkinson Disease" Journal of Biological Chemistry, vol. 287, No. 30, Mar. 22, 2012, pp. 24862-24872.
Kopeikina, K., et al., "Soluble forms of tau are toxic in Alzheimer's disease," Translational Neuroscience 3(3), 2012, pp. 223-233.
Kouzehgarani, G., et al., "Harnessing cerebrospinal fluid circulation for drug delivery to brain tissues," Advanced Drug Delivery Reviews, 2021, vol. 173, pp. 20-59.
Lee, V., et al., "Neurodegenerative tauopathies," Annual Review of Neuroscience, vol. 24, 2001, pp. 1121-1159.
Legon, W., et al., "Transcranial focused ultrasound modulates the activity of primary somatosensory cortex in humans," Nature Neuroscience vol. 17, No. 2, 2014, pp. 322-329.
Lei, P., et al., "Tau protein: relevance to Parkinson's disease," The International Journal of Biochemistry & Cell Biology, vol. 42, Issue 11, 2010, pp. 1775-1778.
Lin, Z., et al., "Facile synthesis of enzyme-inorganic hybrid nanoflowers and their application as an immobilized trypsin reactor for highly efficient protein digestion." (Communication) RSC Adv., 2014, 4, 13888-13891.
Lipsman, N., et al., "Blood-brain barrier opening in Alzheimer's disease using MR-guided focused ultrasound," Nature Communications vol. 9, Article 2336, 2018, pp. 1-8.
Lomen-Hoerth, C., et al., "The overlap of amyotrophic lateral sclerosis and frontotemporal dementia," Neurology, vol. 59, 2002, pp. 1077-1079.
Chinese Office Action for Chinese Application No. 202080041867.5, dated Jul. 12, 2023 (12 pages).
International Search Report and Written Opinion for International Application No. PCT/US23/17893, mailed Jun. 29, 2023 (13 pages).
International Searching Authority, International Search Report for International Application No. PCT/US2024/017736, dated Aug. 19, 2024, together with the Written Opinion of the International Searching Authority, 15 pages.
International Search Report and Written Opinion for International Application No. PCT/US2023/015972, mailed Jul. 27, 2023, 12 pages.
International Preliminary Report on Patentability for International Application No. PCT/US2022/034706 mailed Jan. 4, 2024 (7 pages).
Notice of Reasons for Refusal for Japanese Patent Application No. 2021-560113, with English translation, dated Jan. 4, 2024 (12 pages).
Second Chinese Office Action for Chinese Patent Application No. 202080041867.5, with English translation, dated Apr. 30, 2024 (26 pages).
Extended European Search Report for European Patent Application No. 20788080.8, dated Jun. 4, 2024 (12 pages).
Office Action Decision of Refusal from Japanese Patent Office for application No. 2021-560113 dated Jun. 25, 2024, 5 pages.

Syringe Pump Delivery Module Base Substrate 300

3-Way Flow Diverters 25

Manifold 54

550

Recesses 540

Tube Set Base Substrate 400

Single-Use Flow and Pressure Sensors 29

Diagnostic Module Base Substrate 500

Conduits 14A/14B Extend and Terminate in Lumbar 16B and Ventricle 16B Ports

Forming a CSF circuit that has at least one pump and a catheter — 610

Adding a therapeutic material to the CSF circuit — 620

Flowing, using the pump and the catheter, the patient's CSF through the CSF circuit at one or more flow rates — 630

Monitoring, when CSF is flowing in the CSF circuit, at least one quality of the CSF after adding the therapeutic material to the CSF — 640

Controlling the one or more flow rates of the CSF as a function of the monitored qualities of the CSF — 650

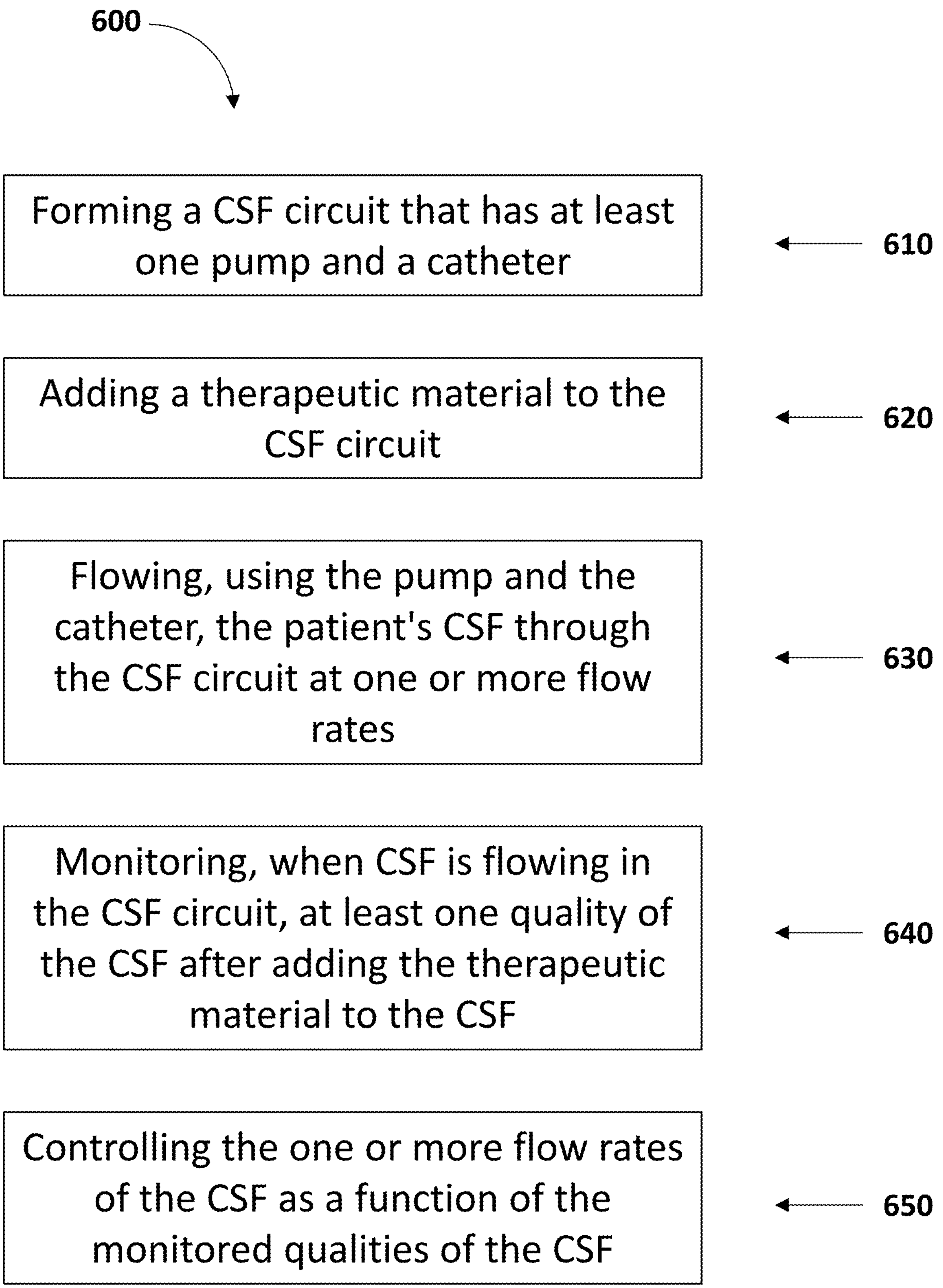

*FIG. 6*

CSF DIAGNOSTICS PLATFORM

PRIORITY

This patent application claims priority from Provisional U.S. Patent Application No. 63/223,248, filed Jul. 19, 2021, entitled, "CSF DIAGNOSTICS PLATFORM," and naming Rajan Patel, Gianna N. Riccardi, and Kevin Kalish as inventors.

This application is also a Continuation-In-Part of U.S. patent application Ser. No. 17/848,211 filed on Jun. 23, 2022, and entitled, "METHOD OF REGULATING GENE EXPRESSION," which claims the benefit of, and priority to, U.S. provisional patent application No. 63/214,239, filed Jun. 23, 2021.

U.S. patent application Ser. No. 17/848,211 is also a Continuation-In-Part of U.S. patent application Ser. No. 17/489,620 filed on Sep. 29, 2021, and entitled, "SUBARACHNOID FLUID MANAGEMENT METHOD AND SYSTEM WITH VARYING RATES," which claims the benefit of, and priority to, U.S. provisional patent application No. 63/084,996, filed Sep. 29, 2020, and U.S. provisional patent application No. 63/117,975, filed Nov. 24, 2020.

U.S. patent application Ser. No. 17/848,211 is also a Continuation-In-Part of U.S. patent application Ser. No. 17/495,682, filed on Oct. 6, 2021, and entitled, "SYSTEM AND METHOD FOR CONTROLLING CSF FLOW AND MANAGING INTRACRANIAL PRESSURE," which claims the benefit of, and priority to, U.S. provisional patent application No. 63/088,401, filed Oct. 6, 2020.

U.S. patent application Ser. No. 17/848,211 is also a Continuation-In-Part of U.S. patent application Ser. No. 17/669,883 filed on Feb. 11, 2022, and entitled "METHODS OF AMELIORATION OF CEREBROSPINAL FLUID AND DEVICES AND SYSTEMS THEREFOR," which is a continuation of U.S. patent application Ser. No. 17/062,440, filed on Oct. 2, 2020, which is a continuation of PCT Patent Application Number PCT/US20/27683, filed on Apr. 10, 2020, which claims priority to and the benefit of U.S. Provisional Patent Application No. 62/832,486, filed on Apr. 11, 2019, and U.S. Provisional Patent Application No. 62/960,861, filed on Jan. 14, 2020.

The disclosures of all of the above noted patent applications are incorporated herein by reference in their entireties, including the drawings and appendices.

FIELD OF THE INVENTION

The present disclosure generally relates to medical devices and methods and, more particularly, relates to devices and methods for recirculation of a fluid, such as cerebrospinal fluid ("CSF"), throughout a body of a patient for diagnosis of neurodegenerative disorders.

BACKGROUND OF THE INVENTION

When diagnosing neurodegenerative disorders, sampling and analysis of patients' CSF can be a valuable tool for attempting to neutralize and/or reverse the effects of the disorder. Sampling and collection of the CSF is a difficult process as various parameters are tracked to ensure no long term damage is being done to the patient while system parameters are tracked to ensure that desired sampling procedures are followed.

SUMMARY OF VARIOUS EMBODIMENTS

In accordance with one embodiment of the invention, a CSF management method for use with a patient having a body with CSF includes forming a CSF circuit that has at least one pump, and catheter. The CSF circuit is configured to channel the flow of the patient's CSF, and adding a therapeutic material to the CSF circuit. The CSF circuit flows the patient's CSF through the CSF circuit at one or more flow rates using the pump and the catheter. When CSF is flowing in the CSF circuit, at least one quality of the CSF is monitored after adding the therapeutic material to the CSF, and the one or more flow rates of the CSF is controlled as a function of at least one of the monitored qualities of the CSF.

The CSF management method may further include determining, as a function of the monitoring, that the concentration of therapeutic material in the CSF is low. Controlling the one or more flow rates of the CSF may include increasing the rate of flow of the patient's CSF through the CSF circuit to decrease the patient's absorption of the therapeutic material.

The CSF management method may further include determining, as a function of the monitoring, that the concentration of therapeutic material in the CSF is high. Controlling the one or more flow rates of the CSF may include decreasing the rate of flow of the patient's CSF through the CSF circuit to increase the patient's absorption of the therapeutic material. Controlling the one or more flow rates may include reversing the flow of the CSF.

The CSF management method may further include adding more therapeutic material to the CSF circuit as a function of the monitoring at least one quality of the CSF. The at least one quality may include one or more of the following: CSF protein levels; osmolarity; pH levels; glucose levels; CSF pressure; IgG; cytokine levels; sodium levels; potassium levels; or magnesium levels. The at least one quality may include the concentration of a biomarker in the CSF and/or the concentration of the therapeutic in the CSF.

The CSF management method may further include disconnecting at least a portion of the CSF circuit to remove control of the flow of the CSF. Disconnecting at least a portion of the CSF circuit may conclude a single CSF session. Controlling includes changing the rate of flow of the patient's CSF before the disconnecting.

The CSF management method may further include disconnecting at least a portion of the CSF circuit to remove control of the flow of the CSF. Disconnecting at least a portion of the CSF circuit may conclude a single CSF session. The controlling may include setting a new rate of flow of the patient's CSF after disconnecting. The new rate of flow may be used during a later CSF session. The controlling may include automatically controlling the one or more flow rates of the CSF as a function of at least one monitored quality of the CSF.

The CSF management method may further include completing a first CSF session and a second CSF session in series. The method may use a first catheter with the first CSF session and a second catheter with the second CSF session. The first catheter and second catheters may be different. The first catheter may not be used during the second CSF session.

The CSF circuit may have a flow-through segment with at least one sensor configured to monitor the CSF. The monitoring may include flowing the CSF through the flow-through segment for analysis by the at least one sensor.

The CSF circuit may include an end segment forming an output port. The output port may be sealable and configured to enable removal of CSF from the circuit.

The CSF management method may further include fluidly coupling a removable sample collection container to the output port. The output port may include a plurality of output ports. The CSF circuit includes at least one flow controller configured to direct CSF flow toward or away from one or more of the plurality of output ports.

The CSF management method may further include fluidly coupling a sampler to the output port, and the sampler may be configured to monitor one or more of the at least one quality of the CSF. The controlling comprises controlling the one or more flow rates of the CSF after receipt of a sample signal from the sampler. The sample signal may have information relating to the at least one quality of the CSF.

In accordance with another embodiment, a CSF management system for use with a patient having a body with CSF and a port to the patient's CSF includes a CSF circuit includes a catheter and a valve system. The CSF circuit is configured to control flow of the patient's CSF and being removably couplable with the patient's port to form a closed fluid flow system. The CSF circuit is accessible via a sealable port. The CSF management system includes a CSF monitor configured to monitor at least one quality of the CSF when the CSF is flowing in the CSF circuit. A flow controller is operatively coupled with the CSF monitor. The flow controller is configured to control the flow rate of the CSF through the CSF circuit as a function of the monitored qualities of the CSF. The CSF management system may further include a pump configured to pump CSF through the CSF circuit. The pump may be a dry pump.

The flow controller may be configured to increase the rate of flow of the patient's CSF through the CSF circuit to decrease the patient's absorption of the therapeutic material when the concentration of therapeutic material in the CSF is below a threshold concentration. The flow controller may be configured to decrease the rate of flow of the patient's CSF through the CSF circuit to increase the patient's absorption of the therapeutic material when the concentration of therapeutic material in the CSF is above a threshold concentration. The flow controller may be configured to reverse or stop the flow of the CSF.

The at least one quality may include one or more of the following: CSF protein levels; osmolarity; pH levels; glucose levels; CSF pressure; IgG; therapeutic material levels; cytokine levels; sodium levels; potassium levels; or magnesium levels. The at least one quality may include the concentration of a biomarker in the CSF and/or the concentration of the therapeutic in the CSF.

The flow controller may be configured to automatically control the one or more flow rates of the CSF as a function of at least one monitored quality of the CSF. The CSF circuit may have a flow-through segment with at least one sensor configured to monitor the CSF for the at least one quality. The sealable port may include an end segment forming an output port, and the output port may be sealable and configured to enable removal of CSF from the circuit.

The CSF management system may further include a removable sample collection container that is removably couplable to the output port. The sealable port may include a plurality of output ports. The flow controller may be configured to cooperate with the valve system to direct CSF flow toward or away from one or more of the plurality of output ports.

The CSF management system may further include a manifold coupled with a plurality of the output ports. The system may further include a plurality of containers that are removably and sealably couplable with the CSF ports.

The CSF management system may further include a sampler configured to fluidly couple with the sealable port. The sampler may be configured to monitor one or more of the at least one quality of the CSF. The flow controller may be configured to control the one or more flow rates of the CSF after receipt of a sample signal from the sampler. The sample signal may have information relating to the at least one quality of the CSF.

Monitoring may occur during a given CSF session and after the given CSF session. Monitoring may include gathering at least one sample of the CSF for off-site analysis after the end of the CSF session.

The CSF management system may further include a base substrate. The base substrate may include a dry pump and a catheter pump interface for operatively coupling with the catheter. The base substrate may include a manifold having a plurality of output ports configured to receive a plurality of containers for CSF, and at least a portion of the valve system to control fluid flow into the manifold. The base substrate may include a sensor region to receive at least a portion of the CSF monitor, and a guide configured to receive and secure at least a portion of the catheter to the base substrate.

The CSF circuit may have a flow-through segment with at least one sensor configured to monitor the CSF for the at least one quality. The CSF management system may further include a base substrate having a dry pump and a catheter pump interface for operatively coupling with the catheter, a sensor region to receive at least a portion of the CSF monitor, and a guide configured to receive and secure at least a portion of the catheter to the base substrate.

In accordance with another embodiment, a medical kit includes a catheter including a body forming a fluid traversing bore. The body has a first end and a second end in fluid communication with the bore. The first and second ends of the body are removably couplable between first and second exterior ports of the patient. The bore being configured to be in fluid communication with both the first and second exterior ports when removably coupled therebetween. The body is configured to form a closed loop CSF channel when removably coupled between the first and second exterior ports. The CSF channel and bore are in fluid communication with the patient's subarachnoid space when the body is removably coupled. The kit includes a valve configured to redirect fluid flow within the CSF channel, and a CSF monitor having a sensor configured to monitor at least one quality of the CSF within the closed loop CSF channel. The kit also includes a flow controller configured to control the flow rate of the CSF through the CSF circuit as a function of at least one monitored quality of the CSF.

The medical kit may further include at least one CSF container configured to removably and fluidly couple with the CSF channel. The medical kit may further include a manifold having a plurality of output ports, and the manifold may be configured to couple with the CSF channel.

The medical kit may further include a flow-through segment that is part of the CSF channel. The flow-through segment may be part of the catheter or separate from the catheter.

The medical kit may further include a therapeutic material reservoir configured to removably couple with the CSF channel. The therapeutic material reservoir may contain a fluid therapeutic material.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 6 shows an embodiment of a CSF management method for use with a patient having a body with CSF in accordance with illustrative embodiments.

DESCRIPTION OF ILLUSTRATIVE EMBODIMENTS

Figure 1A:
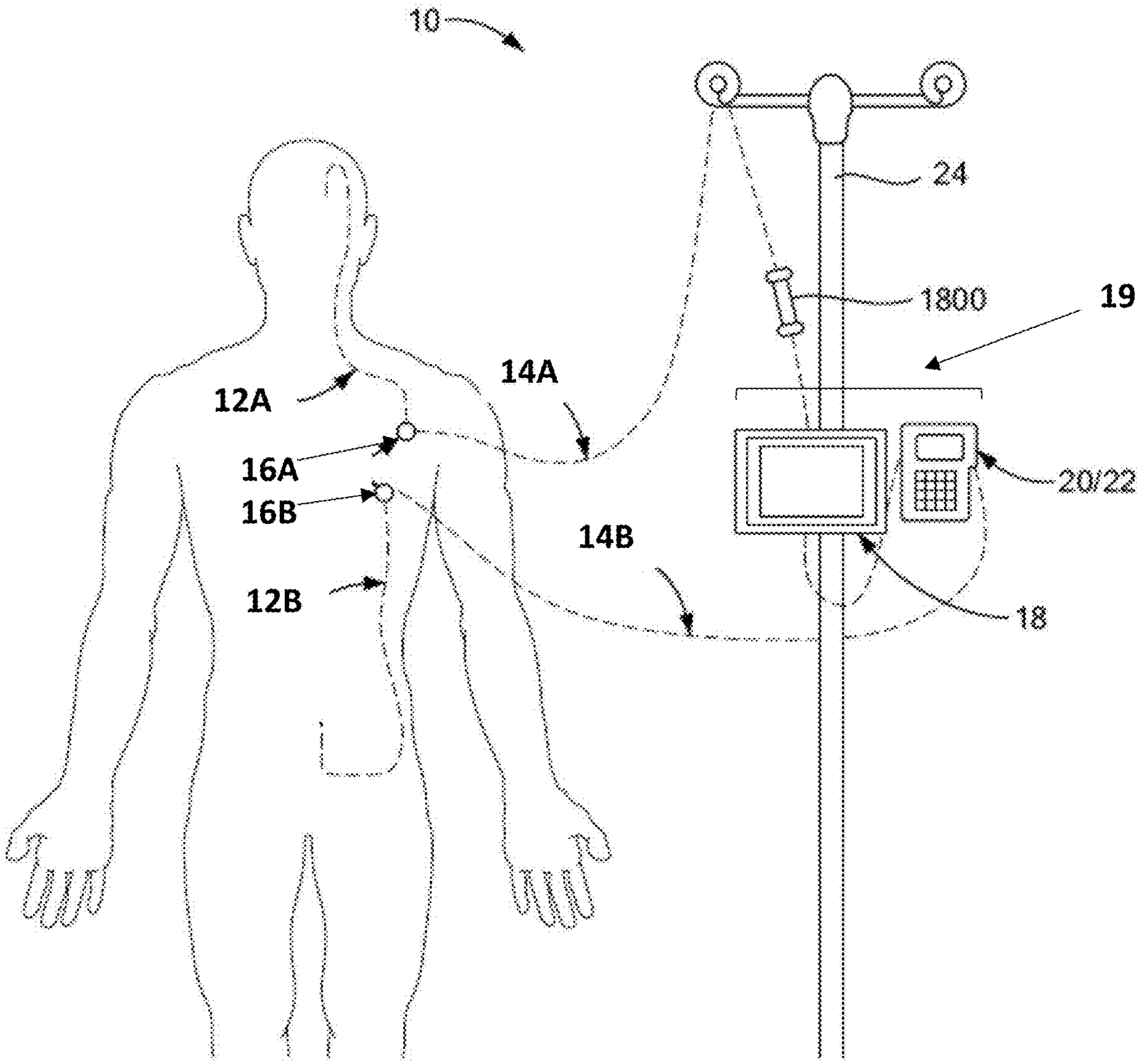
FIG. 1A schematically shows an embodiment of a cerebrospinal fluid circuit that may be used with illustrative embodiments, FIG. 1B schematically shows an embodiment of a portion of a management system for controlling a cerebrospinal fluid circuit that may be used with illustrative embodiments, FIG. 1C schematically shows an embodiment of a cerebrospinal fluid circuit that may be used with illustrative embodiments, FIG. 1D schematically shows an embodiment of a portion of a management system for controlling a cerebrospinal fluid circuit that may be used with illustrative embodiments.

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, compositions, and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

In illustrative embodiments, a system controllably applies a therapeutic material, such as a drug (e.g., methotrexate, a chemotherapy, small interfering RNA (siRNA), microRNA (miRNA), plasmid DNA, messenger RNA (mRNA), small activating RNA (saRNA), splicing-modulatory ASOs, and CRISPR (clustered regularly interspaced short palindromic repeats)/Cas (CRISPR-associated protein, adenoviral vectors (AAV), and immunosuppressive drug) to a specific anatomical location within the subarachnoid space or other area. The therapeutic material, or simply "material", which also may be referred to herein as a "drug," may be applied in a single large volume as a bolus, or dosed gradually over a longer time. To that end, the system has a flow controller (e.g., controller) or control system that manages distribution of the therapeutic material within a CSF circuit through which cerebrospinal fluid ("CSF") flows. Specifically, among other things, the controller (e.g., "flow controller") manages pumps, valves, catheters, and/or other structure(s) to control fluid flow, flow direction, and frequencies of certain periodic flows of bodily fluids (e.g., CSF), to provide a more localized and efficient therapeutic application to a patient.

Preferred embodiments enable the therapeutic material to penetrate the blood-brain barrier by either selecting appropriate CSF and therapeutic material flow rates, and/or controlling CSF flow to maintain a bolus of the therapeutic material within CSF at/near a desired location in the CSF circuit. Consequently, using various embodiments, medical practitioners can be more comfortable applying the appropriate application of the therapeutic in the patient, while reducing toxicity and, in some cases, reducing the need for larger volumes of the therapeutic. Details of illustrative embodiments are discussed below.

Many neurodegenerative diseases have been tied to the accumulation of biomolecules (e.g., toxic proteins) contained in cerebrospinal fluid (CSF) or other fluids (e.g., interstitial fluid) within the subarachnoid space (SAS) of a mammalian subject. Problematically, these (e.g., toxic) biomolecules may be secreted and then transported by the CSF to other cells in the body, which process may occur over the span of years. For example, dipeptide repeat proteins (DPRs) and/or TDP-43 have been implicated in neuronal death in the pathology of amyotrophic lateral sclerosis (ALS, or Lou Gehrig's disease), Alzheimer disease (AD), frontotemporal degeneration (FTD), Parkinson's disease (PD), Huntington's disease (HD), and progressive supranuclear palsy (PSP), to name just a few. Hence, research has focused primarily on the removal of harmful DPRs. Techniques for removing DPRs and/or TDP-43 have included: shunting CSF from the CSF space, diluting the CSF (e.g., with an artificial fluid), administering a drug into the CSF, conditioning the CSF, and/or manipulating CSF flow.

Recent breakthrough techniques for handling this problem include ameliorating the CSF, and treating a neurological disorder by removing or degrading a specific (toxic) protein.

Amelioration, as used in various embodiments, involves systems and methods for ameliorating a fluid in the subarachnoid space (SAS) (e.g., a cerebrospinal fluid (CSF), an interstitial fluid (ISF), blood, and the like) of a mammalian subject, unless otherwise particularly distinguished (e.g., referred to as solely CSF). Representative systems may be completely or partially implanted within the body of the mammalian subject (discussed below). Within the body, the systems and/or components thereof may also be completely or partially implanted within the SAS and exposed to the exterior via a port (e.g., a medical valve that provides selective access to the interior system components). These systems execute processes that may occur entirely in-vivo, or some steps that occur extracorporeally. Illustrative embodiments ameliorate with a CSF circuit, discussed below.

Amelioration, for the purpose of illustration, may include changing the physical parameters of the fluid, as well as digestion, removal, immobilization, reduction, and/or alteration, to become more acceptable and/or inactivation of certain entities, including: target molecules, proteins, agglomerations, viruses, bacteria, cells, couples, enzymes, antibodies, substances, and/or any combination thereof. For example, in some embodiments and applications, amelioration may refer to removing toxic proteins from or conditioning one or more of the blood, interstitial fluid, or glymph contained therein, or other fluid, as well as the impact that this removal has on treating diseases or conditions that affect various bodily functions, (e.g., improving the clinical condition of the patient). Moreover, amelioration may be performed by any one of: digestion, enzymatic digestion, filtration, size filtration, tangential flow filtering, counter-current cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photo-acoustical interactions, chemical treatments, thermal methods, and combinations thereof. Advantageously, various embodiments or implementations of the present invention may reduce levels of toxicity and, after reduced, facilitate maintaining the reduced levels over time.

The extent of amelioration, as reflected by the concentration of the target biomolecules, may be detected through a variety of means. These include optical techniques (e.g., Raman; coherent Stokes, and anti-Stokes Raman spectroscopy; surface enhanced Raman spectroscopy; diamond nitrogen vacancy magnetometry; fluorescence correlation spectroscopy; dynamic light scattering; and the like) and use of nanostructures such as carbon nanotubes, enzyme linked immunosorbent assays, surface plasmon resonance, liquid chromatography, mass spectrometry, circular proximity ligation assays, and the like.

Amelioration may include the use of a treatment system (e.g., UV radiation, IR radiation), as well as a substance, whose properties make it suitable for amelioration. Amelioration of CSF or ameliorated CSF—which terms may be used interchangeably herein—refers to a treated volume of CSF in which one or more target compounds have been partially, mostly, or entirely removed. It will be appreciated that the term removed, as used herein, can refer not only to spatially separating, as in taking away, but also effectively removing by sequestering, immobilizing, or transforming the molecule (e.g., by shape change, denaturing, digestion, isomerization, or post-translational modification) to make it less toxic, non-toxic or irrelevant.

The term, "ameliorating agent" generally refers to a material or process capable of ameliorating a fluid, including enzymes, antibodies, or antibody fragments, nucleic acids, receptors, anti-bacterial, anti-viral, anti-DNA/RNA, protein/amino acid, carbohydrate, enzymes, isomerases, compounds with high-low biospecific binding affinity, aptamers, exosomes, ultraviolet light, temperature change, electric field, molecular imprinted polymers, living cells, and the like. Additional details of amelioration are taught by PCT Application No. PCT/US20/27683, filed on Apr. 10, 2020, the disclosure of which is incorporated herein, in its entirety, by reference. In a similar manner, details for further treatments are taught by PCT Application No. PCT/US19/042880, filed Jul. 22, 2019, the disclosure of which is incorporated herein, in its entirety, by reference.

In illustrative embodiments, a system can include a diagnostic module that has the capability to sample and analyze CSF. The diagnostic module of the presently disclosed embodiments can provide at least two options for diagnostic capability. In some embodiments, CSF can be gathered using a dead-end diagnostic junction that allows the CSF to be gathered in diagnostic segment and sent for off-site analysis. The CSF gathered and analyzed using a dead-end diagnostic segment is removed from the system and not placed back in circulation. The dead-end diagnostic segment may also be designated as an end segment. The sample of CSF gathered may be collected in a removable sample vial (e.g., sample collection container, or end segment), or may be provided by microfluidics to a miniature analysis tool (e.g. a "lab-on-a-chip"). The sample vials may be configured to be coupled to output ports that are sealable and are configured to enable removal of CSF from the circuit. The output ports may be assembled into a manifold that is coupled with the output ports, and containers can be removably and sealably couplable with the CSF ports. Furthermore, the samples may be gathered into a removable sample collection container that is removably couplable to the output port.

Alternatively, or in addition to, in some embodiments, a flow-through diagnostic junction can be used to allow the CSF to be analyzed in-line, and then reintroduced the CSF into circulation. The diagnostic junction may direct the CSF to a flow-through segment of the system.

CSF in either the dead-end diagnostic segment or flow-through diagnostic segment may be analyzed by optical techniques, such as: Raman; coherent Stokes, and anti-Stokes Raman spectroscopy; surface enhanced Raman spectroscopy; diamond nitrogen vacancy magnetometry; fluorescence correlation spectroscopy; dynamic light scattering; and the like.

In illustrative embodiments, the diagnostic module can facilitate analysis of the CSF for the diagnosis of, for example, determining the presence of, and/or a concentration of a therapeutic material (e.g., drug, or material) in the CSF; and, determining the presence of, and/or an amount of biomolecules (e.g., toxic proteins) contained in the CSF or other fluids (e.g., interstitial fluid) within the subarachnoid space (SAS).

A smart diagnostic junction may be mounted on a tube set and can include with two or more 3-way flow diverters (e.g., three way valves) that are disposed within junctions formed therein that can regulate flow through the CSF circulation tubing, as well as direct CSF into the diagnostic module. The system can further include monitoring hardware such as a control board and one or more sensors that attach to one or more system components, or is located outside of the system, to measure intracranial and/or intrathecal pressure.

The smart diagnostic junction is facilitated by a combination (2 or more) of 3-way flow diverters that may be configured to divert CSF to the diagnostic module. Inside the diagnostic module, the CSF may be analyzed in a flow-through manner and/or gathered (e.g., sampled) for removal from the system and measurement. The samples can be collected in vials having an RFID tag thereon to identify variables such as time, quantity, and type of collection method performed. Moreover, similar to automatic collection, a number of valves used for sampling can be increased to increase scalability of the system.

Moreover, in some embodiments, the system can change sampling to occur as a function of a drug being infused into the system rather than as a function of time. For example, a control system can be configured to control a volume of an syringe pump of a drug (e.g., therapeutic material, or just material) being introduced into the system to ensure that adequate pressure and flow rate is maintained in the system. The volume of the drug being introduced can be set and regulated based on the type of drug being introduced to ensure that a safe concentration of the drug is maintained in the system and within the body of the patient.

In some embodiments, the volume of the drug infused into the system can depend on the composition found in the CSF. For example, the system can sample the CSF to detect the type and concentration of toxic biomolecules, e.g., tau, cis p-tau, Abeta, TDP-43, SOD1, DPRs, neurofilaments, and alpha-synuclein, found therein to determine a volume of the drug to introduce into the system that would rid the system of the toxic molecules. The system can then adjust parameters to correspond to the concentration based on principles known to one skilled in the art.

The system can be configured to send an alert when the pressure goes above and/or beyond a certain upper threshold, as well as when the pressure drops below a certain lower threshold. Moreover, in some embodiments, a flow controller can be included to actively monitor in-line pressure and automatically adjust the flow rate in order to maintain CSF flow and prevent an occlusion or significant reduction in flow. Further, the flow controller may also automatically redirect the flow to move in the opposite direction through the CSF circuit.

To control CSF flow within the body (e.g., through the ventricle), illustrative embodiments form a CSF circuit/channel that manages fluid flow in a closed loop. FIG. 1A, for example, shows an embodiment of such a CSF circuit 10. In this example, internal catheters 12A and 12B (also referred to generically as "tubing" or the like) positioned in-vivo/interior to the body fluidly couple together via the subarachnoid space (SAS). To that end, a first internal catheter 12A fluidly couples a prescribed region of the brain (e.g., the ventricle) to a first port 16A, which itself is configured and positioned to be accessible by external components. In a corresponding manner, a second internal catheter 12*b* couples the lumbar region or the lower abdomen of the SAS with a second port 16B that, like the first port 16A, also is configured to be positioned and accessible by external components.

The first and second ports, 16A and 16B, respectively, may be those conventionally used for such purposes, such as a valved Luer-lock or removable needle. The first and second internal catheters, 12A and 12B, respectively, thus may be considered to form a fluid channel extending from the first port 16*a*, to the ventricle, down the spine/subarachnoid space to the lumbar, and then to the second port 16B. These internal components, which may be referred to as "internal CSF circuit components," are typically surgically implanted by skilled professionals in a hospital setting.

The CSF circuit 10 also has external components (referred to as "external CSF circuit components"). To that end, the external CSF circuit components include at least two fluid conduits (e.g., catheters), 14A and 14B. Specifically, the external CSF circuit components include a first external fluid conduit 14A, that couples with the first port 16A for access to the ventricle. The other end of the first external conduit 14A is coupled with a management system 19, which includes one or more CSF pumps (all pumps are generically identified in the figures as reference number "18"), one or more user interface/displays 20, one or more drug pumps 18, and a control system/controller 22. In embodiments, the interface/displays 20 and the control system/controller 22 may be combined into a single unit control system 20/22. In embodiments, the control system/controller 22 may also be described as a flow controller 22, such that the terms are used interchangeably and synonymously. The external fluid conduits 14A and 14B may be implemented as catheters and thus, that term "catheter" may be used interchangeably with the term "conduit" and be identified by the same reference numbers 14A and 14B.

Illustratively, this management system 19 is supported by a conventional support structure (e.g., a hospital pole 24 in FIG. 1A). To complete the CSF circuit 10, a second external fluid conduit 14B extends from that same CSF management system 19 and couples with the second port 16B and the management system 19. This management system 19 and external fluid conduits 14A and 14B therefore form the exterior part of a closed CSF circuit 10 for circulating the CSF and therapeutic material. As used in this disclosure, "therapeutic material" may be used interchangeably with "material." A "material" and a "therapeutic material" may be used to describe a "drug".

It should be noted that the CSF circuit 10 may have one or more components between the first and second ports 16A and 16B and the respective removable connections of the first and second external fluid conduits 14A and 14B. For example, the first port 16A may have an adapter that couples with the first external catheter 14A, or another catheter with a flow sensor may couple between such external catheter 14A and port 16A. As such, this still may be considered a removable connection, albeit an indirect fluid connection. There may be corresponding arrangements with the other end of the first external catheter 14A, as well as corresponding ends of the second external catheter 14B. Accordingly, the connection can be a direct connection or an indirect connection. In embodiments, the CSF circuit 10 may have a cartridge 1800 fluidically coupled in-line with external fluid conduits 14A and/or 14B.

The first and second external fluid conduits 14A and 14B preferably are configured to have removable connections/couplings with the management system 19, as well as their respective ports 16A and 16B. Examples of removable couplings may include a screw-on fit, an interference fit, a snap-fit, or other known removable couplings known in the art. Accordingly, a removable coupling or removable connection does not necessarily require that one forcibly break, cut, or otherwise permanently break the ports 16A and 16B for such a connection or disconnection. Some embodiments, however, may enable a disconnection form the first and/or second ports 16A and/or 16B via breaking or otherwise, but the first and/or second ports 16A and/or 16B should remain in-tact to receive another external fluid conduit 14A and/or 14B (e.g., at the end of life of the removed external catheter 14A and/or 14B, or at the completion of a treatment session).

Figure 1B:
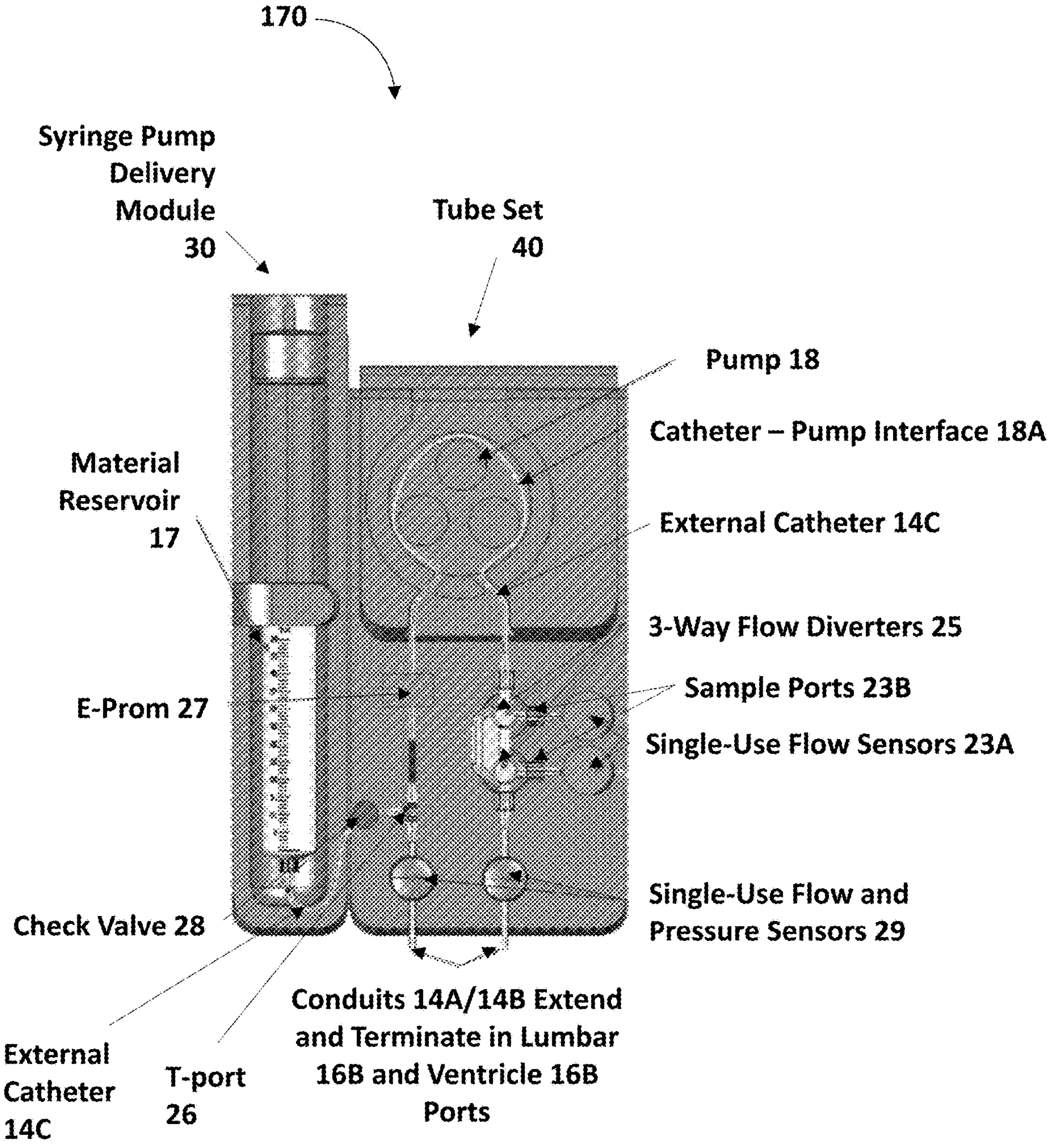
FIG. 1E shows some embodiments of segments for flow-through diagnostics.
FIG. 1F schematically shows an embodiment of a portion of a management system for controlling a cerebrospinal fluid circuit that may be used with illustrative embodiments, FIG. 1G schematically shows an embodiment of a single use feature being mounted to a portion of a management system for controlling a cerebrospinal fluid circuit that may be used with illustrative embodiments, FIG. 2 schematically shows an embodiment of smart diagnostic junction fluid control that may be used with illustrative embodiments, FIG. 3 schematically shows an embodiment of smart diagnostic junction fluid control that may be used with illustrative embodiments, FIG. 4 schematically shows an embodiment of smart diagnostic junction fluid control that may be used with illustrative embodiments, FIG. 5 schematically shows an embodiment of a high level surgical flow process in accordance with illustrative embodiments.

FIG. 1B schematically shows an embodiment 170 of a tube set 40 and a syringe pump delivery module 30. The tube set 40 includes an embodiment of the CSF pumps 18 that pump fluid in the CSF circuit 10 through the first and second external fluid conduits 14A and 14B. In embodiments, pump 18 is a dry pump. That is, CSF fluid does not come into direct contact with components of the pump 18. Instead, the CSF fluid is constrained within external catheter 14C, and the pump 18 components are not wetted (e.g., contacted) by the CFS fluid. External catheter 14C may be coupled with the pump 18 via a catheter pump interface. In some embodiments, pump 18 is a type positive displacement pump used for pumping the CSF fluids contained in external catheter 14C. External catheter 14C is a flexible tube fitted in the catheter-pump interface 18A. In some embodiments, dry pump 18 may be a peristaltic pump, also commonly known as a roller pump.

The external catheter 14C preferably is configured to have different hardness values at different locations. Specifically, illustrative embodiments may use a mechanical/peristaltic pump 18, as shown and noted above. The pump 18 may periodically urge a compressive force along that portion of the catheter 14C it contacts at its interface 18A with the catheter 14C. The outlet of the pump 18 in this case may be the portion of the catheter 14C that is receiving the output of a neighboring compressed catheter portion (e.g., a portion that is adjacent to the compressed catheter portion(s)). To operate efficiently, illustrative embodiments form the catheter 14C to have a specially configured hardness at that location (e.g., a 25-35 Shore A hardness). Diameter also is important for flow and thus, one skilled in the art should determine appropriate diameters as a function of performance and durometer/hardness. Preferably, the portion of external catheter 14*c* that contacts the pump 18 is softer than the remainder of the catheter 14C, although both could have the same hardness. Accordingly, external catheter 14C preferably has a variable hardness along its length and may even have a variable diameter.

FIG. 1B also shows an example of an external catheter 14C operating with other parts of the system 10. A portion of external catheter 14C is configured to fluidically connect at a lower section of a syringe pump delivery module 30. As shown, in this example, syringe pump delivery module 30 is reversibly joined with tube set 40. An optional drug therapeutic material reservoir 17 (e.g., a single-use syringe pump) reversibly integrated into the syringe pump delivery module 30 is configured to deliver a dose of a fluid therapeutic material (e.g., a drug) that fluidly couples with the external catheter 14C, which, in turn, is in fluidic communication with external fluid conduits 14A and/or 14B via check valve 28 and T-port 26 on the external catheter 14C. Check valve 28 is a unidirectional valve controlling the drug infusion from a delivery pump. In some embodiments, the delivery pump is a part of the syringe pump delivery module 30. In addition, the external catheter 14C is coupled with dry pump 18, and also preferably includes sample ports 23B with flow diverters (e.g., 3-way flow diverters) 25 for diverting the circulating the CSF and therapeutic material in external catheter 14C toward or away from sample ports 23B. The sample ports 23B preferably have single use (e.g., sample port) flow sensors 23A to track samples. The sample ports 23B and flow sensors 23A interface with the tube set 40 to calculate the flow and volume of CSF into and out of the diagnostic module Some embodiments may be implemented as a simple fluid conduit (e.g., catheter) having a body forming a fluid-flow bore with removably couplable ends (or only one removably couplable end). Illustrative embodiments, however, add intelligence to make one or both of these external fluid conduits (e.g., catheters) 14A and/or 14B “smart” fluid conduits, effectively creating a more intelligent flow system. For example, either one or both of the external fluid conduits 14A and/or 14B can have a processor, ASIC, memory, EEPROM (discussed below), FPGAs, RFID, NFC, or other logic (generally identified as reference number “27”) configured to collect, manage, control the device, and store information for the purposes of security, patient monitoring, catheter usage, or communicating with the management system 19 to actively control fluid dynamics of the CSF circuit 10. Among other things, the management system 19 may be configured to coordinate with an EEPROM 27 to control CSF flow as a function of the therapeutic material infusion flow added to the CSF circuit 10 (discussed below) via the check valve 28 at the output of the drug reservoir 17.

As shown in FIG. 1B, one embodiment of the external catheter 14C has electrically erasable programmable read-only memory, EEPROM 27, (or other logic/electronics) that can be implemented to accomplish a variety of functions. Among others, the EEPROM 27 can ensure that the CSF circuit 170 and its operation is customized/individualized to a patient, a treatment type, a specific disease, and/or a therapeutic material. For example, in response to reading information stored in the EEPROM 27, the control system 22 may be configured to control fluid flow as a function of the therapeutic material.

Importantly, as a disposable device, the EEPROM 27 or other logic of the external catheter 14C can be configured to provide alerts, and/or produce or cause production of some indicia (e.g., a message, visual indication, audio indication, and the like) indicating that the external catheter 14C has reached an end of its lifecycle, or indicating how much of its lifecycle remains. For example, an external surface of the catheter 14C may have a tag that turns red when the EEPROM 27 and/or other logic 27 determines that the external catheter 14C has reached its full lifetime use. For example, the external catheter 14C may be considered to have a usage meter, implemented as some logic or EEPROM 27, configured to track use of the CSF fluid in external fluid conduits 14A and 14B to help ensure it is not used beyond its rated lifetime. Moreover, the logic or EEPROM 27 can register with the control system 22 to start use timers to reduce tampering or use beyond a lifetime.

Some embodiments have a printable circuit board (PCB) equipped with a wireless interface (e.g., Bluetooth antenna) or a hardware connection configured to communicate with the pump 18 and/or control system 22. The external catheter 14C can be configured to time out after a certain period, capture data, and communicate back and forth with the control system 22 or other off-catheter or on-catheter apparatus to share system specifications and parameters. The external fluid conduits 14A and 14B can be designed to be intelligent flow with proprietary connections such that design of knockoffs or cartridges 1800 (discussed in more detail below) can be prevented to ensure safety and efficacy of the CSF circuit 10 and accompanying processes. The logic in the control system 22 may control various functions of the CSF circuit 10 automatically without the input of a user. That is, controlling intelligent flow, timing out of external catheters, raising and lowering flow rates based on pressure sensor, and the like can be automatically performed by the control system 22 once a treatment session has been initiated, and these functions can be controlled without user (e.g., human) intervention.

In addition to the management logic, the external fluid conduits 14A and 14B also may have a set of one or more flow sensors and/or a set of one or more pressure sensors. In embodiments, the flow sensors may be single-use flow sensors, and may be optionally combined with pressure sensors. Both of those flow sensors are shown generically at reference number 29, and may be located upstream or downstream from their locations in FIG. 1B. For example, the sensor(s) 29, generically shown in FIG. 1B, can be a flow sensor, pressure sensor, or both a flow sensor and pressure. They preferably are positioned between the ports 16A and 16B on the body and the remaining components as shown.

Of course, the flow sensor(s) 29 may be configured to detect flow through the bore of the catheter body, while the pressure sensor(s) 29 may be configured to detect pressure within the bore of the body. Among other functions, the flow sensor(s) 29 may monitor flow rate of fluid through the conduit bore and/or total flow volume through the conduit bore.

Alternative embodiments may provide an open-loop CSF fluid circuit 10. For example, the CSF fluid circuit 10 may have an open bath (not shown) to which fluid is added and then removed. The inventors expect the closed-loop embodiment to deliver better results, however, than those of the open-loop CSF fluid circuit 10.

Illustrative embodiments are distributed to healthcare facilities and/or hospitals as one or more kits. For example, one more inclusive kits may include the internal and external catheters 12A/12B and 14A/14B, respectively. Another exemplary kit may include just the internal catheters 12A/12B and the ports 16A/16B (e.g., for a hospital), while a second kit may have the external catheters 14A/14B and/or a single-use syringe. Other exemplary kits may include the external catheters 14A/14B and other components, such as the management system 19 and/or a CSF treatment cartridge 1800. Still other exemplary kits may contain valves (discussed below and all valves generally identified by reference number 28), internal and external catheters (12A, 12B, 14A, 14B, and 14C, etc.) and other components that may be considered to form a fluid conduit/channel. See below for various embodiments of the CSF circuit 10 and exterior components that also may be part of this kit.

Accordingly, when coupled, these pumps 18, valves (discussed below and all valves generally identified by reference number 28), internal and external catheters (12A, 12B, 14A, 14B, and 14C, etc.) and other components may be considered to form a fluid conduit/channel that directs CSF to the desired locations in the body in a prescribed or controlled manner. It should be noted that although specific locations and CSF containing compartments are discussed, those skilled in the art should recognize that other compartments can be managed (e.g., the lateral ventricles, the lumbar thecal sac, the third ventricle, the fourth ventricle, and/or the cisterna magna). Rather than accessing the ventricle and the lumbar thecal sac, both lateral ventricles could be accessed with the kit. With both internal catheters 12A and 12B implanted, CSF may be circulated between the two lateral ventricles, or a drug could be delivered to both ventricles simultaneously.

Figure 1C:
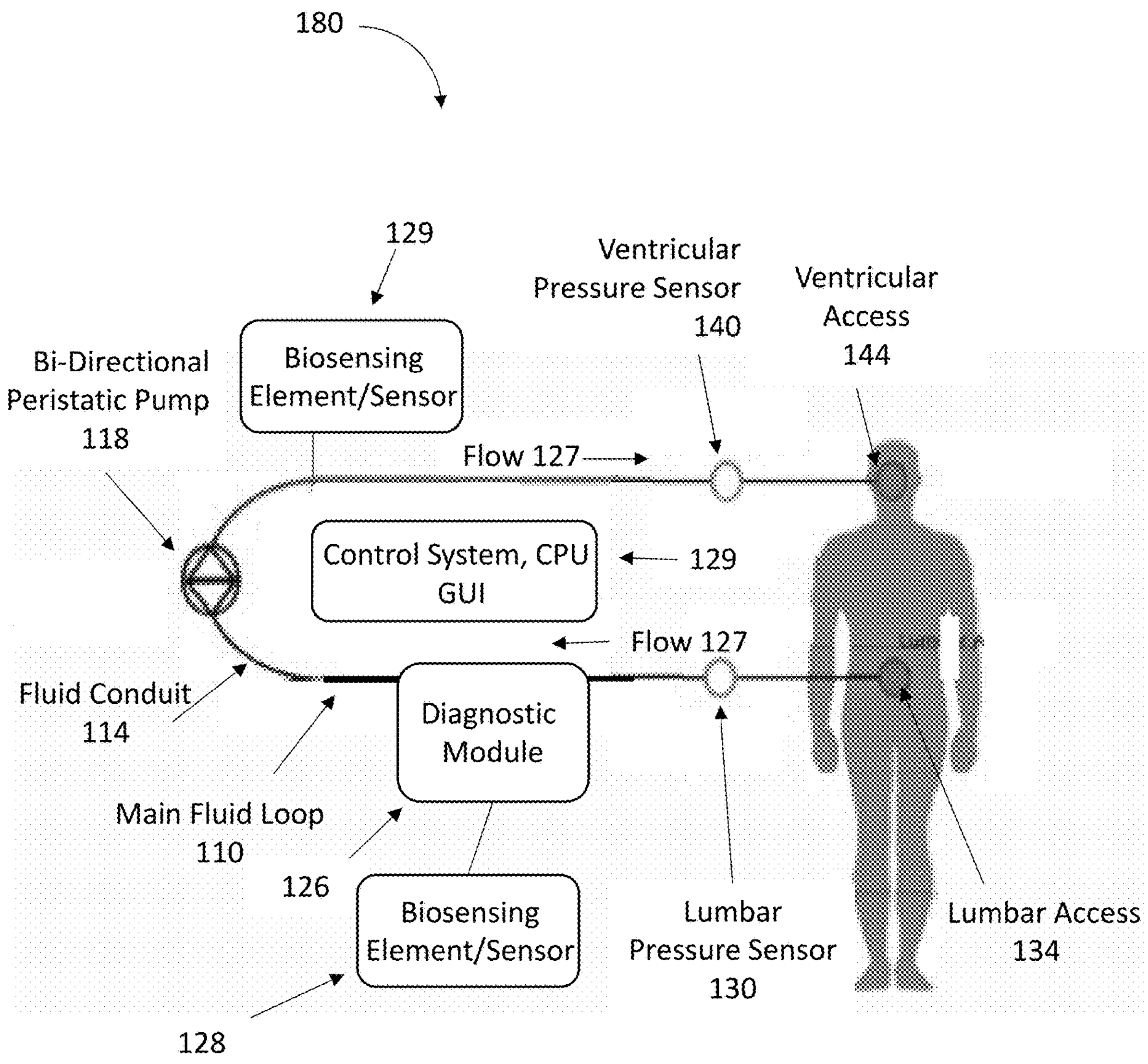

To control CSF flow within the body (e.g., through the ventricle), illustrative embodiments form a CSF circuit/channel that manages fluid flow in a closed loop CSF channel. FIG. 1C, for example, shows an embodiment of such a CSF circuit as a system for gathering and/or sampling CSF. Referring to FIG. 1A and FIG. 1C, in this embodiment, a first catheter 12A accesses the ventricle through a ventricular access 144 in a path coupled with a CSF pump 118 (e.g., dry pump) and CSF management system 19 (e.g., control system). In some embodiments, this pump 118 and control system 19 can be supported by a support structure 24. A second catheter 12B extending from that same CSF pump 118 and control system 19 enters the CSF containing compartment via the lumbar access 134 of the patient or the lower abdomen.

As noted above, also referring to features of FIG. 1A, FIG. 1C illustrates a sample architecture for a system 180 (e.g., fluid management circuit) for automatic sample collection between two catheters, catheter 12A, with ventricular access 144, and catheter 12B, with lumbar access 134, disposed in the body of the patient. As shown, the system 180 can utilize a bi-directional pump 118 to flow CSF through the system. For example, a lumbar catheter 12B and a ventricular catheter 12A can be implanted in the body and connected with the bi-directional pump 118 (e.g., dry pump) via circulation tubing in the main fluid loop 110 to flow a fluid therebetween. To that end, fluid management circuit 180 has at least one pump that directs flow of the CSF, and at least one pump that directs flow of a therapeutic material (e.g., a drug) though the CSF circuit and to a desired anatomy. Alternative embodiments may have more pumps for these functions, or combine a pump for these functions. The pump 118 can exert a force through the tubing of the main fluid loop 110 to promote flow of the CSF from the lumbar catheter 12B to the ventricular catheter 12A, though it will be appreciated that in some embodiments the pump 118 can be configured to flow CSF in the opposite direction. These catheters may be considered to form a fluid conduit that directs CSF to the desired locations in the body. It should be noted that although specific locations and CSF containing compartments are discussed, those skilled in the art should recognize that other compartments can be managed (e.g., the lateral ventricles, the lumbar thecal sac, the third ventricle, the fourth ventricle, and/or the cisterna magna). Rather than accessing the ventricle and the lumbar thecal sac, both lateral ventricles can be accessed with standard catheters. With both catheters 12A and 12B implanted, CSF can be circulated between the two lateral ventricles, or a drug could be delivered to both ventricles simultaneously.

The fluid management circuit 180 can include a control system 129 that works with the pump 118 to manage fluid flow to target anatomy through the CSF circuit. In embodiments, the control system 129 is a part of management system 19. For example, in some embodiments, the control system 129 can regulate the flow rate, pressure, and/or direction of the flow of CSF through the main fluid loop 110. The control system (e.g., control board) can include a CPU processor and a graphic user interface (GUI) for inputting and/or measuring system parameters. The control system 129 can be configured to vary one or more system settings automatically in response to the system parameters. For example, if the pressure of the CSF flowing through the system decreases, the control system 129 can increase a flow rate to counteract the pressure drop. Alternatively, if the pressure of the CSF flowing through the system increases, the control system 129 can decrease a flow rate to counteract the pressure increase. It will be appreciated that the system settings can be varied to improve patient safety. In some embodiments, the control system 129 can redirect flow paths to momentarily cycle within the system 180 without pulling and/or pushing from the patient. Alternatively, or in addition, the control system 129 can create a pause or stoppage of flow throughout the fluid management circuit 180, along with an alert to inform a user that flow has been ceased. The alert can be a signal, noise, color, whistle, email or text message, or another form of notification known by one skilled in the art to inform regarding the occurrence of an event. Some additional non-limiting examples of system settings that can be varied by the control board can include a pressure, a temperature, or a flow rate of the fluid, among others.

In some embodiments, users input rules for the control system 129 to follow. For example, users can program a rule to raise flow rate and/or pressure as desired during sampling and/or to increase a flow rate such that a loss in pressure is offset when samples are taken. The control system 129 can then execute the rule to ensure that sampling is performed as desired without detriment to the patient.

The system 180 can include one or more pressure sensors in communication with a diagnostic module 126, which can create a feedback loop through the system. For example, fluid that flows through the diagnostic module 126 can be pumped through a lumbar pressure sensor 130 and a ventricular pressure sensor 140 prior to flowing out through the ventricular catheter 12A. The pressure sensors 130,140 can measure the pressure of the fluid traveling therethrough to determine an amount of CSF that was withdrawn from the system for sampling. As shown, the pressure sensors 130, 140 can be connected to the control system 129 to inform the user continuously and in real-time about the pressures of the CSF traveling therethrough. Additionally, the pressure sensors 130,140 can be connected to the control system 129 to provide the control system 129 with input that can be used to control the system 180 automatically.

It will be appreciated that when removing fluid from the patient, whether for sampling or analyzing and recirculating, a pressure drop can be experienced within the system, and the patient. A drop in pressure can be dangerous for the patient as insufficient levels of CSF in the body can cause paralysis and even death. If a rapid drop in pressure is detected by either of the sensors 130,140, the control system 129 can be configured to automatically adjust to counteract the pressure drop to alleviate the situation for the patient. For example, in some embodiments, when a pressure drop is sensed, the control system 129 can automatically increase the flow rate of the fluid flowing through the system 180 to reduce the pressure drop. To increase the flow rate, the control system 129 can send a signal to the pump to increase the flow of fluid through the tubing of the system. Under normal conditions, a flow rate of about 0.05 ml/min to about 25 ml/min of CSF through the system is expected to maintain a safe pressure therein, though in some embodiments, flow rates of about 0.05 ml/min to about 15 ml/min, about 0.05 ml/min to about 5 ml/min, or about 0.05 ml/min to about 2 ml/min are used. It will be appreciated that the feedback loop of the system can also decrease flow rate when the pressure increases to undesirable levels. Furthermore, the feedback loop provides inputs to the control system 129 based on monitoring the various sensors and the diagnostic module so that the control system may automatically control the pump 118, valve settings, and the like of the system 180. The automatic controlling of the pump takes place without direct user intervention. That is, the control system may be pre-programmed by a user to monitor the various sensors and the diagnostic module 126, and to receive inputs from the various sensors and the diagnostic module 126, so that that the pre-programmed control system 129 can incorporate those inputs to automatically control the system.

Further regarding FIG. 1C, in embodiments, the fluid management circuit 180 of this disclosure may include a diagnostic module 126, which may form an additional pathway for liquid matter traveling through all aspects of the device, and this fluid may not access the patient. That is, the diagnostic module 126 may include a fluid circuit that does not return to a port (e.g., an access point). Referring also to FIG. 1A, in embodiments, the diagnostic module 126 circulates the mixed CSF and therapeutic material through a fluid conduit (e.g. catheter) integrated into the management system 19, including the pumps 18 and the control system 20/22.

As shown in FIG. 1C, the fluid management circuit 180 includes a main fluid loop 110 that circulates a mixed CSF/material through a fluid conduit 114 from a lumbar access 134 around the main fluid loop 110 to the ventricular access 144. As shown, the main fluid loop 110 exits the patient from the lumbar access 134 to the lumbar pressure sensor 130 flowing in a flow direction 127. The impulse for the flow proceeds from bi-directional dry pump 118. In embodiments, bi-directional pump 118 (e.g., dry pump) may flow the mixed CSF/material in a direction opposite to the direction of flow 127. The bi-directional pump 118 may be any kind of pump that can drive the fluid flow in either direction and whose components are not wetted (e.g., contacted) by the CFS fluid (as described above for dry pump 18).

The diagnostic module 126 is fluidically connected to the main fluid loop 110, and can circulate the mixed CSF/material through a circuit that permits diagnosis and measurement of various aspects of the CSF fluid in a flow-through orientation, and/or in a dead-end orientation. In this way, the CSF may undergo diagnoses outside of the body and during a treatment session of the patient, and the measurements/diagnosis may be used to provide control of the flow quality of the fluid management circuit 100. That is, during a course of treatment, qualities of the CSF may be measured, and the results of the measurement may be used by a user, or may be used by the controller to automatically modify flow conditions.

The measurements/diagnosis may be made by an optional biosensing element (e.g., sensor) that can measure qualities of the CSF. The biosensing element/sensor may be present in one or both of the main fluid loop 110 (as biosensing element/sensor 129), and/or in the diagnostic module 126 (as biosensing element/sensor 128).

In order to monitor/measure the CSF in the flow-through segment, the diagnostic module 126 may have the optional biosensing element 128 (e.g., sensor). In embodiments, the diagnostic module 126 may include a flow-through orientation that allows the CSF to flow through the diagnostic module 126, and the CSF may optionally be flowed back into the fluid management circuit 100. The CSF may be flowed through a sample chamber, such as a cuvette, that permits the biosensing element/sensor 128 to measure qualities of the CSF. The sample chamber of the flow-through segment provides optical access to the CSF so that monitoring/measuring sensors may characterize one or more qualities of the CSF. Measuring the CSF may also be referred to monitoring one or more qualities of the CSF.

The biosensing elements 128/129 may be one or more of a flow sensor, a temperature sensor, a pressure sensor, a pH sensor, a spectrophotometer, or a photo sensor. The terms sensors, sensor elements, biosensor elements, and biosensor elements/sensors, as used in this disclosure, are interchangeable, are described in greater detail below. The biosensing element/sensor 128/129 may be present in one or both of the main fluid loop 110 (as biosensing element/sensor 129), and/or in the diagnostic module 126 (as biosensing element/sensor 128).

Qualities of the CSF that may be monitored/measured include detection of a biomarker, a concentration of a biomarker, a detection of a therapeutic material (e.g., drug), a concentration of a therapeutic material, a pressure of the CS a flow rate of the CSF, a pressure of the CSF, a temperature of the CSF, and the like.

In particular, specific biomarkers may also be observed, quantified, and diagnosed by one or more biosensing elements 128/129. Specific biomarkers that may have therapeutic relevance include brain proteins, hormones, IgG, cytokines, sodium, potassium, magnesium, and anything that has the potential to be found in CSF.

Furthermore, there are additional qualities that may be measured and/or monitored in the CSF, including:

Osmolarity (e.g., specific gravity) of serum and CSF. The osmolarity is known to be 1.024-1.028 and 1.004-1.007, respectively, the estimated average of osmolarity (mOsm/L) in the serum and CSF covered exactly the same range (i.e., 290.5-291.5 mOsm/L). Monitoring and control of osmolarity is crucial, because hyperosmolar CSF is sufficient to produce a proportional degree of hydrocephalus in the normal rat brain.

pH levels of serum and CSF. pH levels can be used to determine an amount of an infection. For example, a slight drop in a pH value during infection may correlate with cell and bacterial number in CSF.

Oxygen levels in CSF. The oxygen levels in CSF, as measured by $pO_2$ (normal levels being 25-53 mmHg in humans), may be used ischemia in spinal cord.

Glucose levels in CSF. A low glucose level (e.g., hypoglycorrhachia) in the CSF can suggest bacterial, fungal, or tuberculous meningitis.

Protein levels in CSF. An abnormal protein level in the CSF may indicate a problem in the central nervous system. Increased protein level may be a sign of a tumor, bleeding, nerve inflammation, or injury. A blockage in the flow of spinal fluid can cause the rapid buildup of protein in the lower spinal area. Low levels of protein in CSF may also indicate a CSF leak. High protein levels may indicate meningitis.

Sodium levels in CSF. Cerebrospinal fluid (CSF) and brain tissue sodium levels increase during migraine.

Chloride levels in CSF. All salts will affect osmolarity

White blood cell count in CSF. If the white blood cell count in CSF is higher than 5 white blood cells per $mm^3$, it constitutes pleocytosis and can indicate inflammation or infection.

CSF pressure. Increased CSF pressure can indicate obstruction, infection, injury.

Glycine and/or lactate levels in CSF. High glycine concentration disrupts temperature and blood pressure control. CSF lactate and/or glycine are calculated also in children when in born errors of metabolism are suspected, although abnormal levels may not be specific for these conditions. CSF lactate may also be used to investigate mitochondrial CNS disease CSF protein 14-3-3 levels in CSF. CSF protein 14-3-3 levels are used as a biomarker of rapid neurodegeneration typically seen in classic Creutzfeldt-Jakob disease, and together with S-100β as a marker of gliosis, are used alongside other investigations to increase the sensitivity of this diagnosis.

Hypocretin levels in CSF. Low CSF hypocretin levels in CSF are associated with narcolepsy.

Rhinorrhoea and/or otorrhoea levels in CSF. CSF leaks giving rise to CSF rhinorrhoea or otorrhoea may also be differentiated from other types of fluid by opportunistic collection and subsequent analysis for tau protein.

Aβ42, total-tau (t-tau), and phosphorylated-tau (p-tau) levels in CSF. The three CSF biomarkers, Aβ42, total-tau (t-tau), and phosphorylated-tau (p-tau) have been found to have the highest diagnostic potential) for Alzheimer's disease.

Brain proteins such as tau and beta amyloid levels in CSF.

Fluid biomarker levels in CSF. α-synuclein levels in CSF are particularly diagnostic in patients with Dementia with Lewy Bodies and other α-synuclein-related disorders.

Neurofilament protein levels in CSF: Among 10,059 individuals in this cited systematic review and meta-analysis, Neurofilament protein L was elevated in most neurological conditions compared with healthy controls, and the magnitude of the increase varies extensively. Although levels overlap between most clinically similar conditions, its distribution did not overlap in frontotemporal dementia and other dementias or in Parkinson disease and atypical parkinsonian syndromes. As a marker of neuronal damage, it may be useful to differentiate some clinically similar conditions, such as frontotemporal dementia from Alzheimer disease and Parkinson disease from atypical parkinsonian syndromes.

Inflammatory and oxidative stress biomarkers. Inflammatory and oxidative stress biomarkers are potential Parkinson's disease.

Cytokine levels in CSF. Increased levels of multiple cytokines (26/36) in patients with neuro-inflammatory diseases when compared to NIND that consistently correlated with CSF cell count and QAlbumin. Under conditions of neuro-inflammation, multiple CSF cytokines are regulated in parallel and most likely produced locally. A combined increase of CSF CXCL13 levels and B cells occurs under conditions of an intact BBB. Under conditions of a disrupted BBB, CSF NK cells show significantly increased values and seem to have a major contribution to overall inflammatory processes, reflected by a strong correlation with multiple cytokines.

Returning to the diagnostic module 126, in embodiments, the diagnostic module 126 may have a dead-end orientation that allows the gathering of CSF in an end segment (e.g., sample vial), and/or a micro-measurement device, such as a lab-on-a-chip. Dead-end junctions direct CSF to a dead-end segment which allows for a sample of CSF to be removed from the diagnostic module 126 on the fluid management circuit 180 for analysis. By removing a sample of CSF from the fluid management circuit, it is possible to monitor a sample of CSF in equipment that may not be available for integration into the diagnostic module 126, or the fluid management circuit 180. The dead-end segments also allow for CSF to be stored for characterization at a remote location, and for the sample to be stored for later study. In embodiments, samples that have been gathered may be sent for off-site analysis for monitoring, such that to monitor a sample includes gathering at least one sample of the CSF for off-site analysis after the end of the CSF session.

A collection of dead-end segments may be provided on the diagnostic module by a manifold to allow for collection of CSF samples over a period of time at predetermined time intervals. By collecting CSF samples at a predetermined time intervals over a duration of time, it is possible to determine an effectiveness of a treatment. This way, it is also possible to determine how the concentration of a therapeutic material (e.g., drug) or the amount of a biomarker changes over a treatment session (e.g., session). Furthermore, by collecting and storing CSF samples, it may be possible to compare CSF samples from one session to another, and from one day to another. The comparisons of CSF samples whether during a session in real-time, or following a session, may both be referred to as monitoring the CSF.

In embodiments, the CSF and the material may be circulated independently. The CSF and the material may be mixed prior to, or during circulation. Samples of CSF and/or mixed CSF/material may be removed from the diagnostic module 126. In embodiments, the flow direction of the diagnostic module 126 may be reversible.

The diagnostic module 126 may circulate a mixed CSF/material (e.g., containing one or more of CSF, therapeutic material, and/or saline) and may have flow rates greater than those of main fluid loop 110. In embodiments, the main fluid loop 110 may have flow rates between from 0.0-100 mL/min. In embodiments, the main fluid loop 110 may have flow rates between 0.1-20.0 mL/min. Flow rates may go below 0.1 mL/min to 0.0 mL/min to maintain safety. At 0.0 mL/min, active flow has stopped.

Excess fluid (CSF/therapeutic/saline) in the main fluid loop 110 and in the fluid diagnostic module 126 may be removed from the main fluid loop 110 and from the fluid diagnostic module 126 via passive flow, or pump, to a reservoir for safety purposes. This fluid may or may not re-enter recirculation via active re-introduction through an active reservoir.

Referring still to FIG. 1C, the main fluid loop 110 may include optional biosensing elements/sensors 128 and 129. The optional biosensing element/sensor 128 may be the same as, or different than optional biosensing element/sensor 129.

Main fluid loop 110 includes ventricular pressure sensor 140, and enters the body of the patient to reach ventricular access 144. The main fluid loop 110 continues through the body of the patient as the mixed CSF/material is delivered to the brain past the blood brain barrier (e.g., BBB) into the volume of the cerebrospinal space (e.g., the brain ventricles and the cranial and spinal subarachnoid spaces). Thus, the CSF is ameliorated by treatment with the material.

Figure 1D:
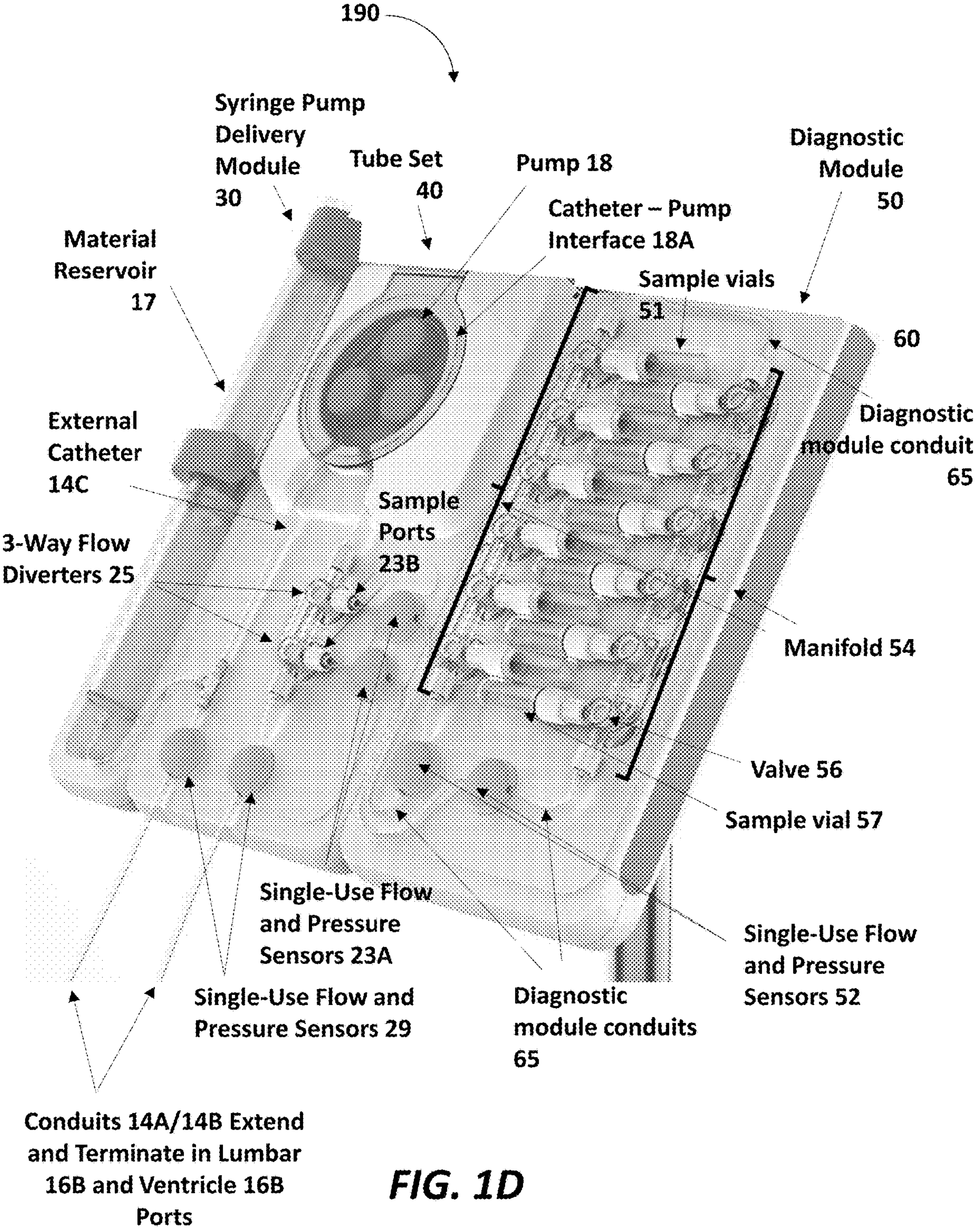

FIG. 1D schematically shows an embodiment 190 of a tube set 40, a syringe pump delivery module 30, and a diagnostic module 50. The descriptions of the tube set 40 and the syringe pump delivery module 30, including reference numbers, as used in FIG. 1D are consistent with those of FIB. 1B. Therefore, the description of FIG. 1D will not include repetition of the description the items present in FIB. 1B. In the embodiment shown in FIG. 1D, the diagnostic module 50 is configured to facilitate dead-end orientations.

In embodiments, the diagnostic module 50, as shown in FIG. 1D (and FIGS. 1A and 1C), is in fluidic communication with the tube set 40 through 3-way flow diverters 25 and sample ports 23B. Diagnostic module conduits 65 fluidically couple to the sample ports 23B through the single-use flow and pressure sensors 23A. On the diagnostic module 50, the diagnostic module conduits 65 are fluidically coupled with the single-use flow and pressure sensors 52. A collection of sample vials 51 (e.g., end segments) may be assembled into a manifold 54. The manifold 54 is in fluidic communication with 3-way flow diverters 25 and sample ports 23B, and fluidically connects together the main fluid loop 110 with the end segments of the manifold 54.

As an example of flow of CSF through the diagnostic module 50, CSF may be pumped by dry pump 18 through external catheter 14C into 3-way flow diverters 25, through sample ports 23B and single-use flow and pressure sensors 23A into diagnostic module conduits 65. The CSF may be further pumped through single use flow and pressure sensors 52 up to the collection of sample vials 51 in the manifold 54. In an embodiment, a portion of CSF may flow through valve 56 and be diverted into sample vial 57 (e.g., end segment). When sample vial 57 has been filled to a predetermined amount, the controller may direct the CSF flow to another valve for diversion into another sample vial. In some embodiments, the valves are actuated by servo motors located in the diagnostic module 50. CSF may likewise be directed to flow of CSF into consecutive sample vials until the manifold 54 has had its sample vials filled to the predetermined amount. This process of diverting the CSF flow to each dead-end segment/sample vial may continue until all of the sample vials are filled, or until the user determines that the process should end. In embodiments, the flow of CSF may proceed along the parallel conduits of the manifold 54 with valve/sample vial pairs, or the flow may be directed to fill along one of the conduits and then directed into the other (parallel) diagnostic module conduit 65.

Figure 1E:
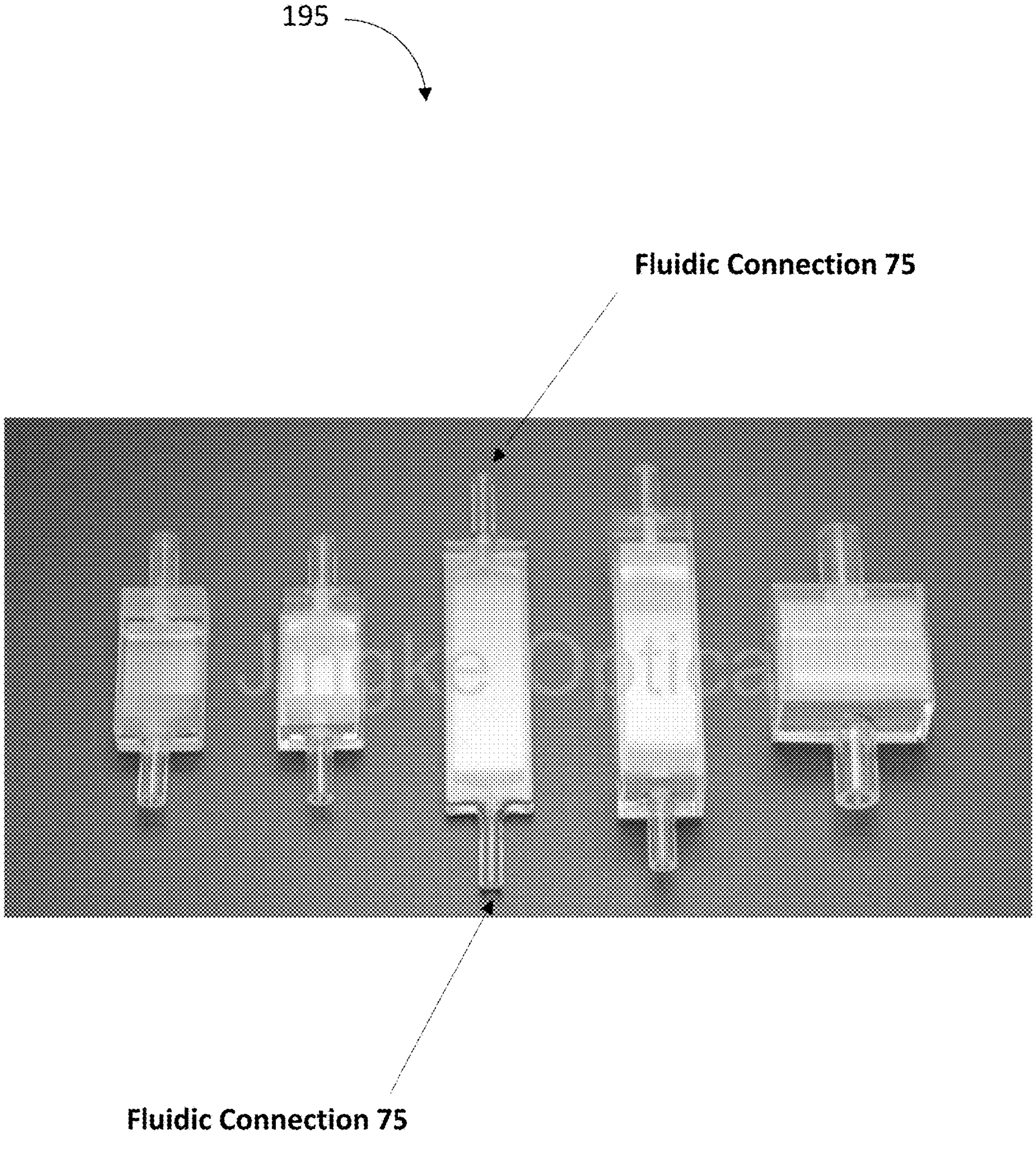

In some embodiments, a flow-through orientation may be provided as part of the diagnostic module 50 (not shown in FIG. 1D). A flow-through segment may be in fluidic communication with a cuvette. FIG. 1E shows some embodiments of cuvettes 195, which may also be known as sample chambers. The cuvettes 195 are configured with different form factors to accommodate different sensors (e.g., biosensing elements/sensors). In embodiments, the cuvettes 195 are configured to be in fluidic communication through fluidic connections 75 with the diagnostic module 50 to allow CSF to enter/exit at one fluidic connections 75 and to enter/exit through another fluidic connections 75.

The sample ports 23B preferably have single use (e.g., sample port) flow sensors 23A to track samples. The sample ports 23B and flow sensors 23A interface with the tube set 40 to calculate the flow and volume into and out of the diagnostic module 50. The flow CSF can be monitored in the diagnostic module 50, and the measurements can be sent to the control system/controller 22 so that the control system/controller 22 can provide instructions to the dry pump to either increase, decrease, or stop the flow of CSF.

Figure 1F:
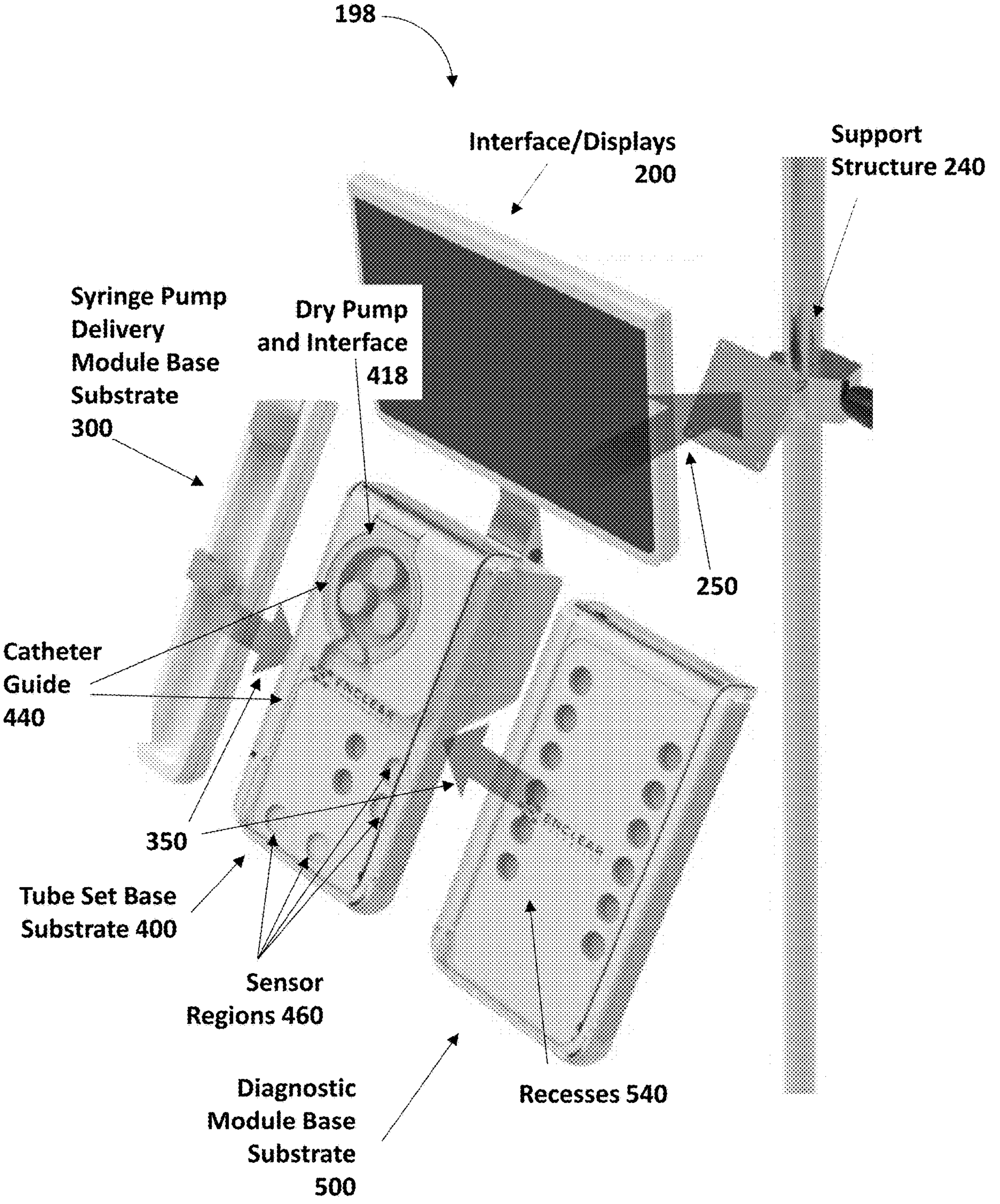

FIG. 1F schematically shows an embodiment of base substrates of a cerebrospinal fluid circuit that may be used with illustrative embodiments a. The syringe pump delivery module 30, the tube set 40, and the diagnostic module 50, as illustrated in FIG. 1D, may include base substrates that are separate structures that can be obtained separately and reversibly assembled together, as shown in FIG. 1F. The base substrates are configured to be durable housings that can provide structure upon which the various catheters, valves, sample collectors, ports, and the like, may be mounted. In some embodiments, the various catheters, valves, sample collectors, ports, and the like are single-use attachments (e.g. disposable) that are temporarily mounted on the base substrates. The single-use nature of the various catheters, valves, sample collectors, ports, and the like, allows for increased sanitation and ease of use by medical staff (e.g. users.)

FIG. 1F shows a syringe pump delivery module base substrate 300, a tube set base substrate 400, and a diagnostic module base substrate 500 that may be reversibly assembled together as illustrated by arrows 350. The base substrates 300, 400, and 500 are configured with recesses into which the single-use attachments may be mounted. Also shown is an embodiment of an interface/display 200. FIG. 1F also shows a support structure 240 upon which the base structures and the interface/display 200 may be mounted, as shown by arrow 250.

Tube set base substrate 400 has dry pump 218 integrated into the base substrate 400, as well as catheter guides 440 and sensor regions 460. The diagnostic module base substrate 500 has recesses 540 into which a manifold may mount. The catheter guide 440 is configured to receive and secure at least a portion of the catheter to the base substrate.

Figure 1G:
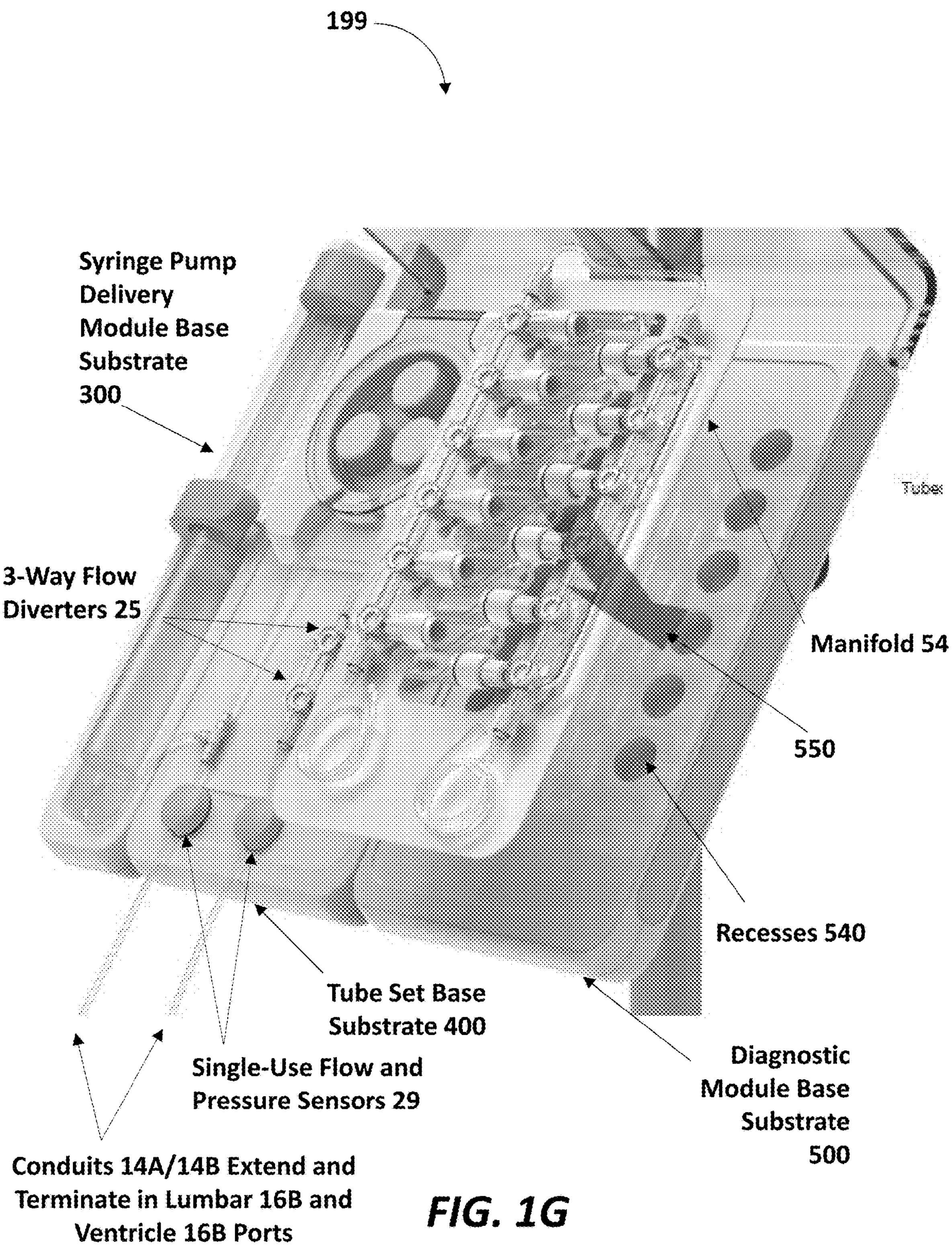

FIG. 1G illustrates an embodiment of deploying a manifold 54 onto a diagnostic module base substrate 500 into the recesses 540, as indicated by arrow 550. In embodiments, manifold 54 is reversibly attached to tube set base structure 400, and is single-use. Syringe pump delivery module base structure 300 is reversibly attached to tube set base structure 400. Tube set base substrate 400 is shown with single use flow and pressure sensors 29, conduits 14A/14B, and 3-way flow diverters 25. In embodiments, the manifold 54, the pressure sensors 29, the conduits 14A/14B, and the 3-way flow diverters 25 may all be single-use attachments that may be disposed of after being used in conjunction with a treatment.

Combinations of 3-way flow diverters may function as smart diagnostic junction mechanical fluid control valves. In some embodiments, the two 3-way flow diverters (e.g., 25 on FIGS. 1B, 1D, and 1G) form a smart diagnostic junction. Each 3-way valve includes a T-junction and a valve. The T-junctions can include one or more branches or conduits that are in the shape of a "T," with each branch being configured to allow the fluid to flow therethrough. It will be appreciated that while T-junctions are illustrated and discussed within the present disclosure, the shape of the junctions is merely exemplary and are intended to convey a branching of the flow of fluid from the main branch. The combination of the two valves allows the fluid management system to operate in three states of flow.

A control system can be used to regulate flow of the CSF through the T-junctions. For example, the control system (e.g., control board) can be used to regulate an orientation of one or more valves (e.g., stopcocks) that are disposed in the T-junctions. The control system can regulate flow automatically such that the valves switch into predetermined orientations in keeping with a set of rules or actions performed or preprogrammed by a user. For example, the valves can be toggled back and forth between configurations automatically according to algorithms of the system, though in some embodiments, the system can respond in real-time to user inputs to alter flow patterns therethrough. For example, an orientation of the valve can be changed based on a user input or automatically according to preprogrammed instructions, with various orientations of the valves discussed in greater detail below.

Depending on the setting of each of the two valves, it is possible recirculate the CSF through the closed CSF circuit without diagnostic engagement with the diagnostic module. This is a default arrangement. In another setting, the valves may be set to direct the CSF through the diagnostic module in a flow-through arrangement so that the CSF may be monitored without being removed from the closed CSF loop. In yet another setting, the valves may be set to direct a portion of the CSF to the diagnostic module in a dead-end arrangement so that portions of the CSF may be collected into end segments, while allowing the remaining portion of the CSF to recirculate through the fluid management circuit.

The valve can be a stopcock valve, though in some embodiments, the valve can be a pinch valve, a butterfly valve, a ball valve, and/or a manifold. The valves can be connected to, and controlled by, a motor to trigger collection of fluid passing therethrough. Each motor can control a single valve, though, in some embodiments, a plurality of motors can be used to control a single valve or a single motor can control a plurality of valves. Some non-limiting examples of motors can include a stepper motor, such as a 90-degree stepper motor, a brushed direct current (DC) motor, or a brushless DC motor, servo-motors, AC motors, synchronous motors, asynchronous motors. In some embodiments, a computer software or program can run an algorithm that controls the positions and timing of the movements of the valves.

In embodiments, the fluid conduit through which the CSF travels from the 3-way flow inverters to the diagnostic module pass through flow sensors that may measure flow rate and/or pressure of the CSF. These flow-through sensors can convey sample volumes to the user via the graphic user interface of the system to inform the user regarding the measured volume of CSF collected or sent through the T-junction to the diagnostic module. For example, samples can be taken using a lower branch of a T-junction without disturbing overall flow of the CSF through the junction towards the pressure sensors of the overall system. These sample volumes can be measured using sensors located at the lower branch of the T-junction past the sample ports 23B (as seen in FIG. 1B) and passed to the control system for analysis and computations to determine whether to change system parameters.

In some embodiments, the T-junctions can include a dead-end orientation in which the valve is rotated with respect to the default configuration. One or more of the valves can be rotated, translated, and/or otherwise moved into an orientation such that a portion of the flow from the lumbar catheter branches off into the lower branch of the T-junction, for example. In such embodiments, CSF is withdrawn from the system without recirculation or reintroduction back into the system. Dead-end sampling can be used in instances in which the withdrawn fluid may be contaminated and therefore recirculation is not desired. It will be appreciated that, in some embodiments, movement of the valves can be controlled by inputs and/or rules of the control system.

A dead-end orientation can be used for sample collection and/or for microfluidics or lab-on-a-chip embodiments. The dead-end orientation can be programmable such that the valves release a desired amount of CSF volume onto a reader chip that can be used in point of care applications. In some embodiments, the results can be read mid-procedure, with a live feed providing information about how the drug is working while it is getting delivered, and/or allowing for adjustment of the delivery based on the live feed. The dead-end orientation can direct flow of the CSF into a manifold having one or more sample vials therein for collection of samples of various volumes and at certain times, along with other parameters set by the user. Furthermore, a dead-end orientation can direct flow of the CSF into a sample collection container having one or more sample vials therein for collection of samples of various volumes and at certain times, along with other parameters set by the user. Some non-limiting examples of such parameters can include timing of each sample taken, quantity of each sample, quality of each sample, and/or patient data during each sample taken, (e.g., blood pressure, intracranial pressure (ICP), lumbar pressure, drug infused, CSF Filtered, physician notes, patient complaints of discomfort, such as headache, back pain, dizziness), directional changes and timing of said directional changes, and/or flow rate. A person skilled in the art will recognize that while a first T-junction may be shown having a valve in the dead-end orientation, in some embodiments, the second T-junction can be oriented to cause branching of the flow of the CSF.

Figure 2:
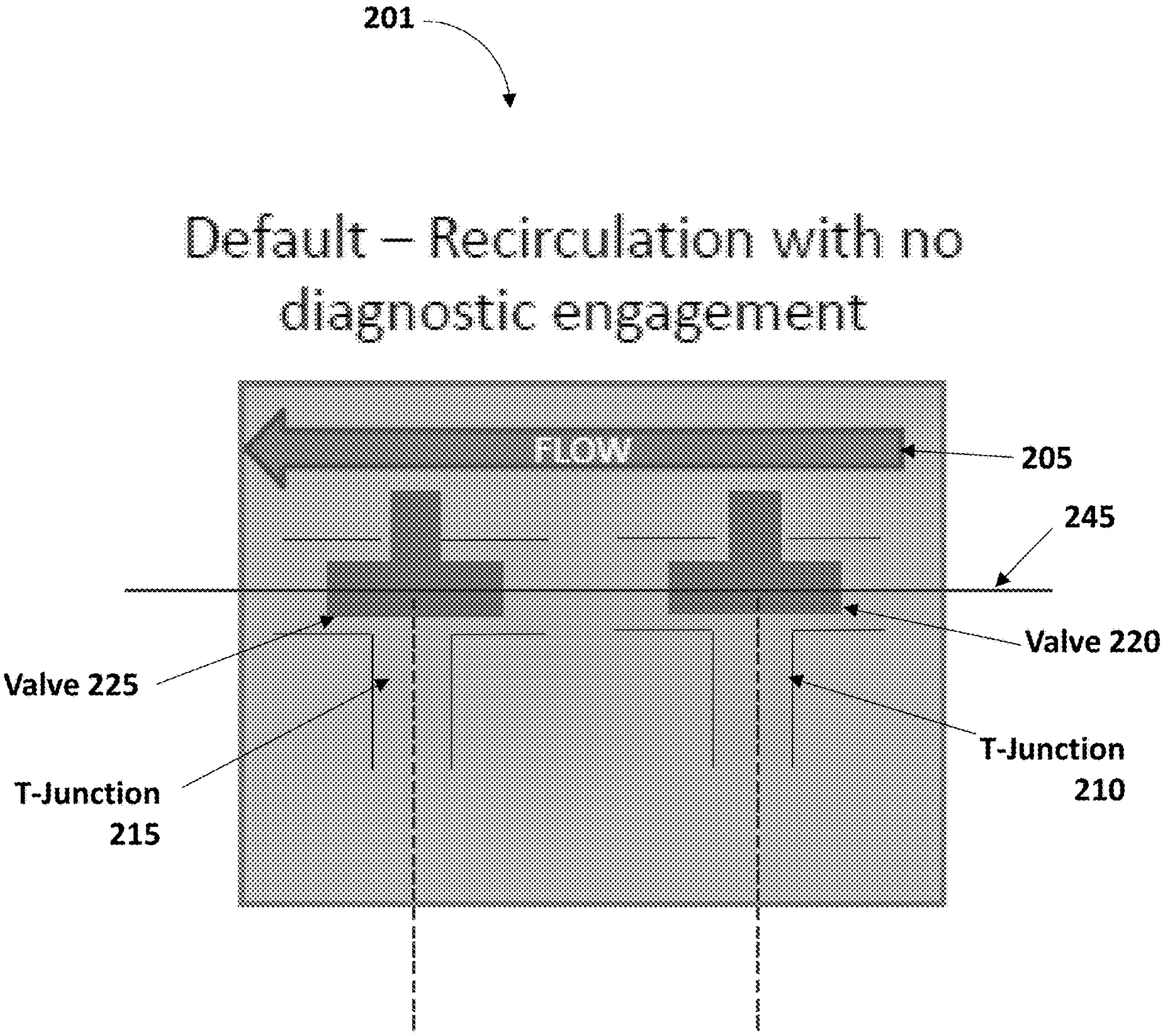

FIG. 2 schematically illustrates valve settings 201 of the two 3-way flow diverters (e.g., 25 on FIGS. 1B, 1D, and 1G) for the smart diagnostic junction to maintain the direction of the CSF through the main fluid loop without passing through the diagnostic module. In FIG. 2, the flow direction of the CSF is indicated by flow arrow 205. The two 3-way diverters each have a T-junction 210, 215 and a valve 220, 225. In the setting 201 illustrated in FIG. 2, each valve 220, 225 is aligned such that the CSF flows through the valves following the solid line 245. This is the default setting that allows CSF to circulate through the fluid management circuit in a closed loop CSF channel without flowing through the diagnostic module.

Figure 3:
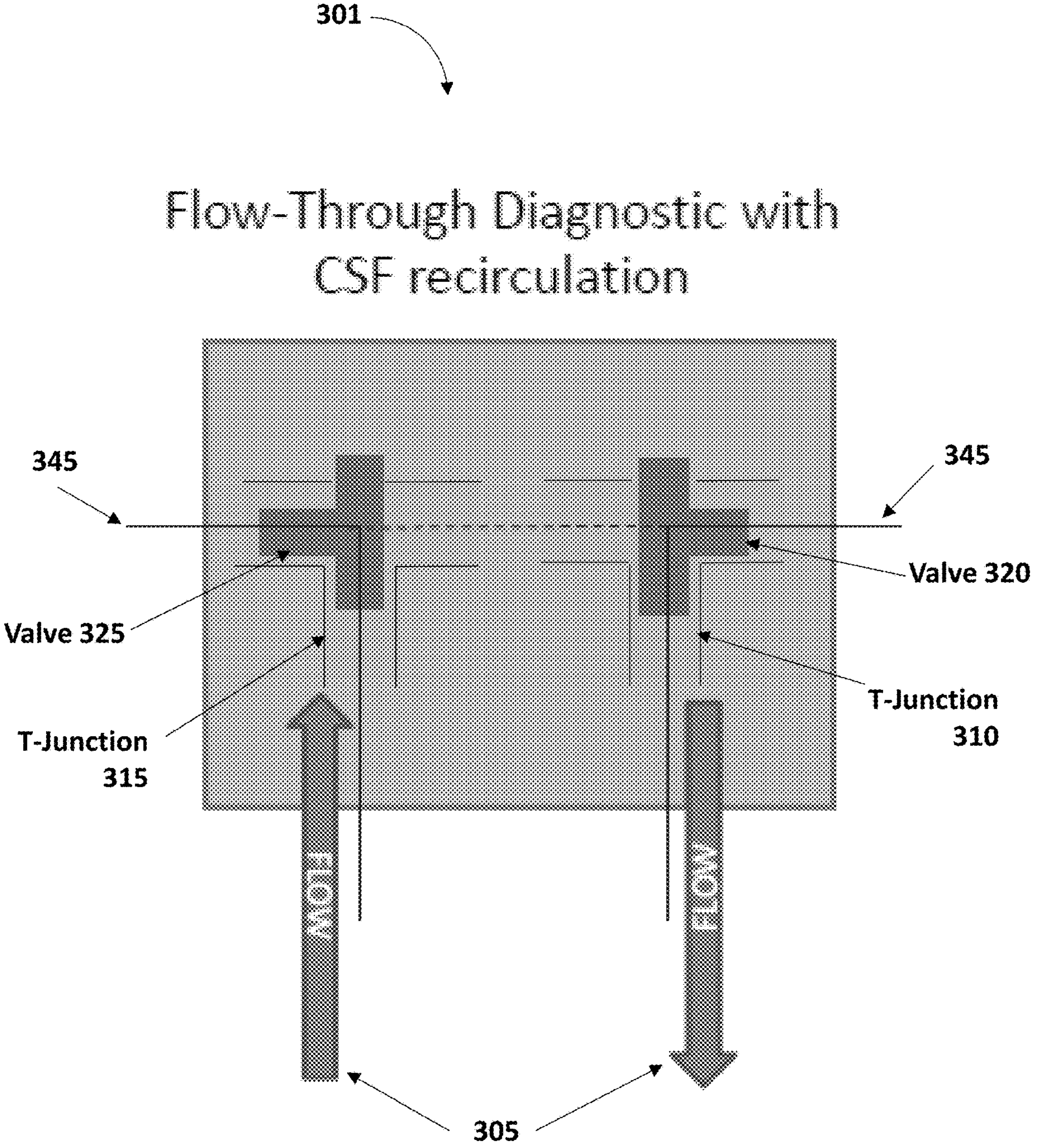

FIG. 3 schematically illustrates an embodiment of the valve settings 301 of the two 3-way flow diverters (e.g., 25 on FIGS. 1B, 1D, and 1G) of the smart diagnostic junction that may be set to direct the CSF through the diagnostic module in a flow-through orientation so that the CSF may be monitored without being removed from the closed CSF loop. In FIG. 3, the flow direction of the CSF is indicated by flow arrow 305. The two 3-way diverters each have a T-junction 310, 315 and a valve 320, 325. In the setting 301 illustrated in FIG. 3, each valve 320, 325 is aligned such that the CSF flows through the valves following the solid line 345. The CSF flow 305 is directed by valve 320 to the diagnostic module such the CSF flow goes into the diagnostic module though T-junction 310 and exits the diagnostic module through T-junction 315. Valve 325 is configured to direct the flow of the CSF back into circulating through the fluid management circuit after flowing through the diagnostic module.

Figure 4:
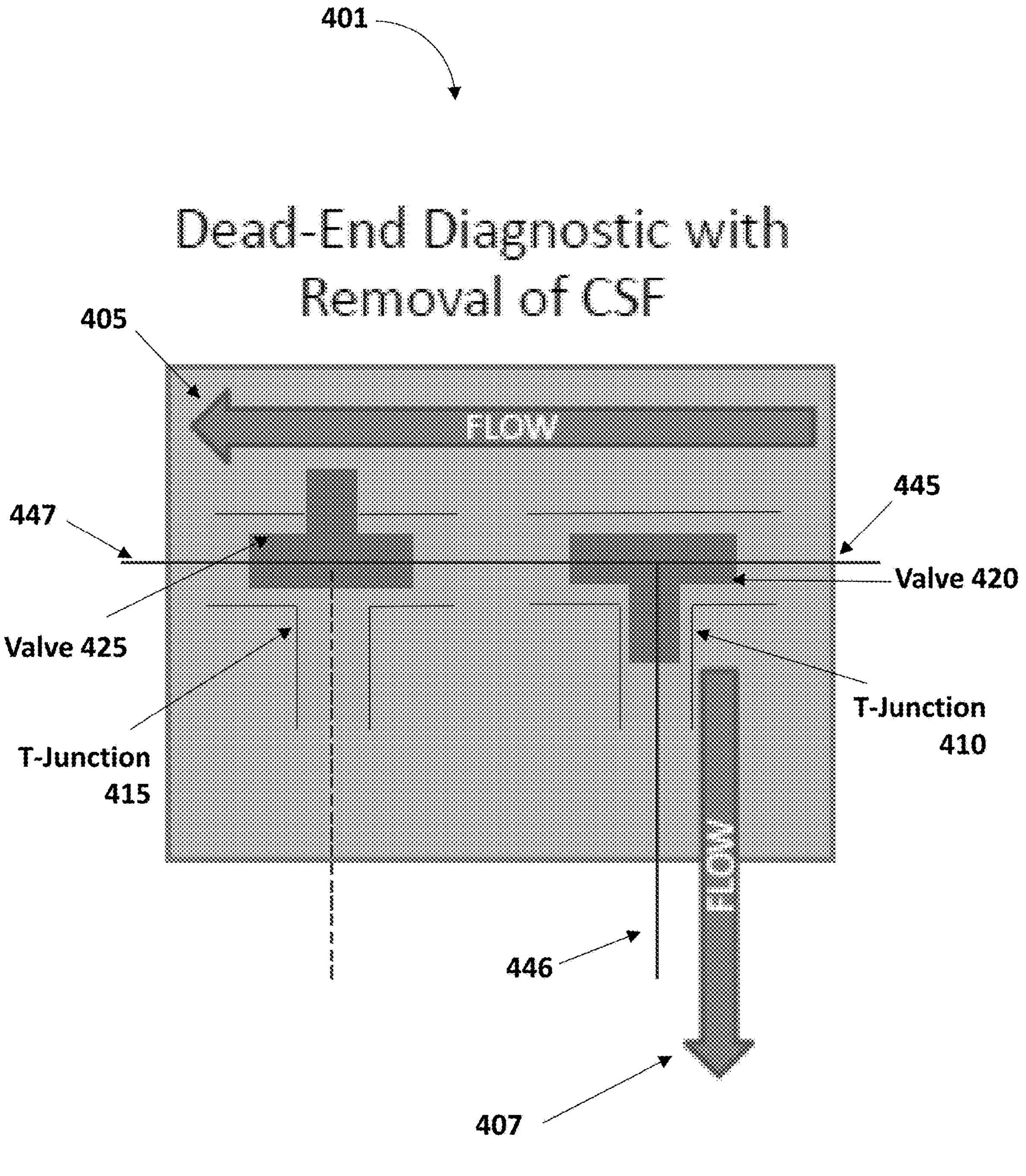

FIG. 4 schematically illustrates an embodiment of the valve settings 401 of the two 3-way flow diverters (e.g., 25 on FIGS. 1B, 1D, and 1G) of the smart diagnostic junction that may be set to direct a portion of the CSF into the diagnostic module, and to direct the remaining portion to flow through the fluid management circuit. In this arrangement, the portion of CSF directed to the diagnostic module may be collected and removed from the fluid management system for analysis. In FIG. 4, the flow direction of the CSF is indicated by flow arrows 405 and 407. The two 3-way diverter valves each have a T-junction 410, 415 and a valve 420, 425. In the setting 401 illustrated in FIG. 4, each valve 420, 425 is aligned such that a portion of the CSF flows through the valves following the solid line 445. A portion of the CSF flow (407) is directed by valve 420 to the diagnostic module such the CSF flow goes into the diagnostic module though T-junction 410 and is collected in end segments and removed from the fluid management circuit. The remaining portion of the CSF flow (405) is directed by valve 420 to continue to circulate through the fluid management circuit by passing through valve 425 in T-junction 415.

In some embodiments, the presently disclosed system may use a monitoring process, such as real-time spectroscopy, to monitor drug concentrations in the CSF. This monitoring may be performed by a biosensing element/sensor on a sample CSF in a flow-through orientation and/or in a dead-end orientation. Additional sensors may include pH sensing, viscosity sensing, temperature sensing, turbidity sensing, and/or osmotic sensing. In some of these embodiments, a spectrophotometric sensor may be placed in the CSF circuit of the system to measure the localized concentration of a substance based on its absorption at various wavelengths. For example, some embodiments may use a sensor capable of measuring a single wavelength or multiple wavelengths. The reading taken by the sensor may be relayed to the controller (e.g., management system) where it would then be stored or processed for various purposes. This signal could be processed for a number of purposes, such as to automatically trigger the controller to alter the fluid flow, flow direction, and/or frequencies of certain periodic flows of bodily fluids (e.g., CSF) to provide a more localized and efficient therapeutic application to a patient in real-time. It will be appreciated that the signal could also be stored or displayed such that the changes to flow, direction or frequencies of period flows could be adjust manually.

Figure 5:
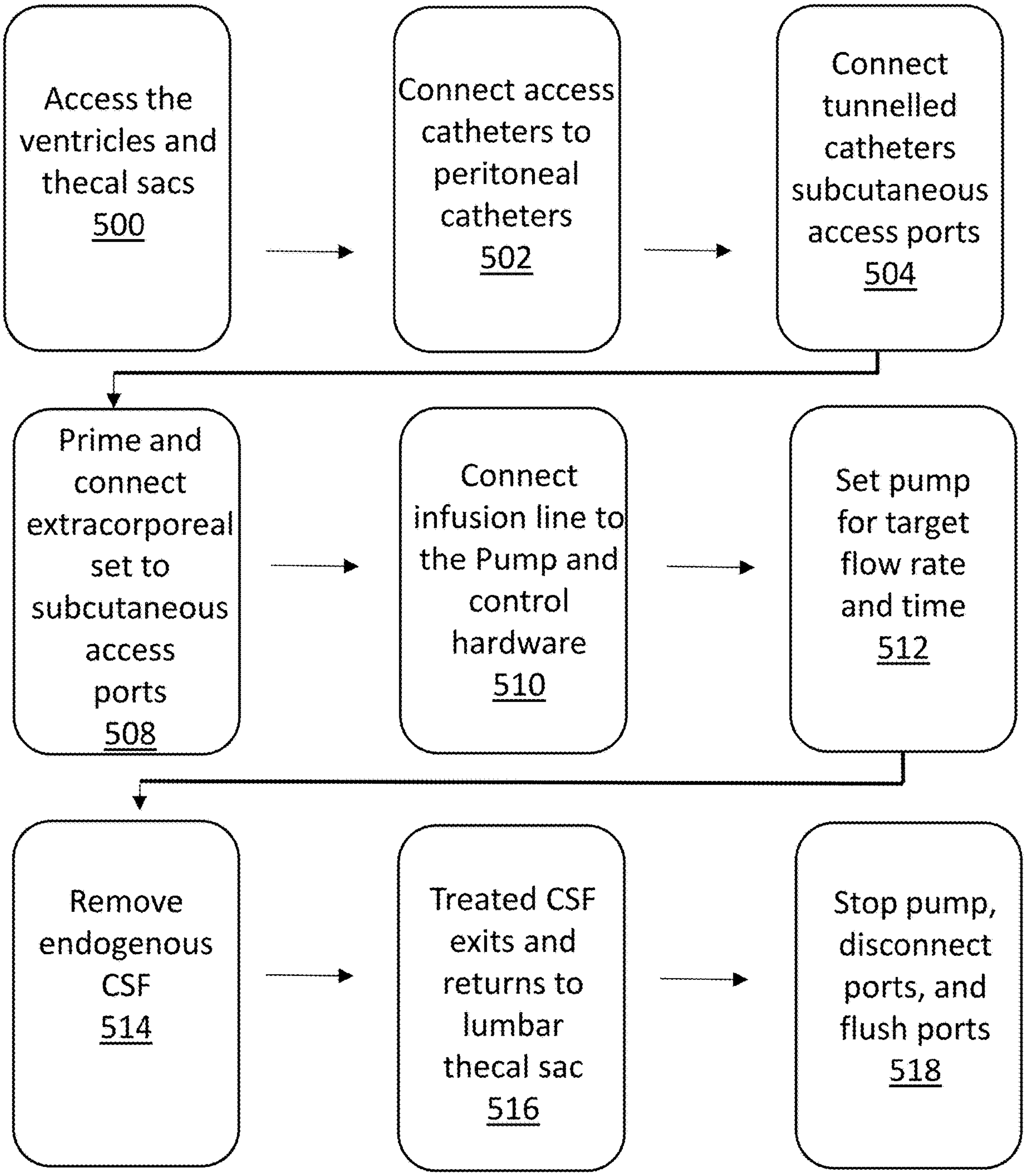

FIG. 5 shows a high level surgical flow process that may incorporate the CSF circuit 10 of FIG. 1A in accordance with illustrative embodiments of the invention. It should be noted that this process is substantially simplified from a longer process that normally would be used to complete the surgical flow. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 500 by setting up the internal catheters 12A,12B inside the patient. To that end, step 500 accesses the ventricles and thecal sacs using standard catheters and techniques, thus providing access to the CSF. Step 502 then connects access catheters to peritoneal catheters 12B, which are tunneled subcutaneously to the lower abdomen. The tunneled catheters 12B then are connected at step 504 to the ports 16B implanted in the abdomen.

At this point, the process sets up an extracorporeal circulation set (e.g., the external catheters 14A,14B, or the "smart catheters" in some embodiments). To that end, step 506 may prime and connect the extracorporeal circulation set 14A,14B to the subcutaneous access ports 16A,16C. Preferably, this step uses an extracorporeal circulation set, such as one provided by Endear Therapies, Inc. of Newburyport, MA, and/or the external catheters 14A,14B discussed above. The process continues to step 510, which connects an infusion line or other external catheter 14A,14B to the management system 19, and then sets the target flow rate and time. At this point, setup is complete and treatment may begin (step 512).

The process then removes endogenous CSF from the ventricle. This CSF may then be passed through a digestion region (e.g., through a cartridge 1800 having a specific digesting material), where certain target proteins in the CSF are digested. For example, the cartridge 1800 may have an inner plenum space 1830 of the cartridge 1800 filled with a plurality of (e.g., porous, chromatography resin) beads that have been compression packed. To prevent constituents from entering or escaping from the cartridge 1800, a filter membrane may be disposed at the first end of the cartridge 1800 and a second filter membrane may be disposed at the second end of the cartridge 1800. In some applications, the ameliorating agent may be decorated on the beads 1835.

In some applications, the cartridge 1800 may be compression packed with a chromatography resin (e.g., agarose, epoxy methacrylate, amino resin, and the like) that has a protease covalently bonded (e.g., immobilized) to the three-dimensional resin matrix. The selected protease may be configured to degrade and/or removing target toxic biomolecules by way of proteolytic degradation. The resin may be a porous structure having a particle size commonly ranging between 75-300 micrometers and, depending on the specific grade, a pore size commonly ranging between 300-1800 Å. Thus, at a high level, the cartridge 1800 has ameliorating agent that removes and/or substantially mitigates the presence of toxic proteins from the CSF.

This and similar embodiments may consider this to be an input for the digesting enzyme. Any location providing access to the drug may be considered to be an input for the drug. At step 516, the treated CSF exits the digestion region and is returned via the CSF circuit 10 to the lumbar thecal sac. The process concludes at step 518, which stops the pump 18 when treatment is complete. The management system 19 then may be disconnected and the ports 16A,16B flushed.

In embodiments, a CSF treatment session (e.g., single session) described above for high level surgical flow process may incorporate the CSF circuit 10 of FIG. 1A. For example, a session may include all of the steps described In FIG. 5. That is, a single session may proceed from the step accessing the ventricles and thecal sacs (500) through to stopping the pump, disconnecting the ports, and flushing the ports (518). In some embodiments, a session may simply be defined by the administration of a given therapeutic material over a given duration. Further, a session may be defined by the duration of time required for a quality of the CSF or a concentration of a therapeutic material to achieve a predetermined quality or concentration, respectively.

In some embodiments, a patient may be treated with more than one session. In that case, a patient may have a first session that may be defined by a first set of instructions, such as, a first therapeutic material, at a first flow rate, for a first duration, a first pressure, and/or a first concentration of the therapeutic material. The first session may be deemed to be complete by a user when one or more of the first set of instructions is achieved. Further, the session (e.g. the first session) may be deemed to begin with connecting external catheters and end when the catheters are disconnected.

In some embodiments, the patient may be treated with a second session. The second session may be defined by a second set of instructions, such as, a second therapeutic material, at a second flow rate, for a second duration, a second pressure, and/or a second concentration of the therapeutic material. The second session may be deemed to be complete by a user when one or more of the second set of instructions is achieved. Further, the session (e.g. the second session) may be deemed to begin with connecting external catheters and end when the catheters are disconnected. One or more of the first set of instructions may be the same as the second set of instructions. Alternatively, there may be no instructions that are same between the first set of instructions and the second.

In accordance with illustrative embodiments, the CSF circuit 10 is configured to improve the likelihood of the drug passing through the blood-brain barrier. To that end, the management system 19 enables the user or logic to independently set both the flow rate of CSF circulation (e.g., between 0.05 ml/min and 2.0 ml/min, such as 0.5 ml/min) and the dosing rate of the drug (e.g., between 0.01 ml/min to 2.0 ml/min, such as 0.02 ml/min). Preferably, these rates are different, although they can be the same. In illustrative embodiments, the CSF circulation rate is controlled to be different from the natural CSF flow rate. Note that the natural CSF flow rate is the rate of CSF flow without intervention by outside equipment, such as the pumps 18 and other CSF circuit components—even if it is within a range of typical non-interventionally controlled CSF flow rates. Thus, unless the context dictates otherwise, the non-natural CSF flow rate is the flow rate with such intervention. In other embodiments, the CSF flow rate is simply changed from its truly natural flow rate—e.g., the rate at which the CSF flows without intervention.

Depending on a number of factors, the CSF flow rate may be greater than the rate of drug infusion, while in other embodiments, the CSF flow rate is less than rate of the drug infusion rate. Other embodiments may set them to be equal. Those skilled in the art can select the appropriate flow rate based on a variety of factors, including the drug being delivered, the illness, patient profile, rated pressure of the CSF circuit 10, etc.

The inventors recognized that varying the two rates in a coordinated manner enables more control of the drug dose as well as more control of the drug treatment time. Stated another way, these two independent flow rates enable setting of the dosing rate, which allows the user to optimize drug concentration. At the same time, having the ability to set the flow rate allows the user to control the rate of delivery (as opposed to relying upon natural CSF flow).

As noted in the example below, the inventors were surprised to discover that varying the rates in this manner enabled penetration of the drug across the otherwise difficult to penetrate blood-brain barrier. The selected CSF flow rate may be constant or variable. For example, the CSF flow rate may be set to a first rate for a first period of time, a second rate for a second period of time, and a third rate for a third period of time. As such, various embodiments enable flow of the CSF within the CSF circuit 10 at two or more flow rates at two or more different times. The drug delivery rate may be constant or variable in a similar manner, but coordinated with the CSF flow rate to deliver preferred results.

FIG. 6 illustrates an exemplary method 600 of a CSF management method for use with a patient having a body with CSF. The method 600 begins at step 610 by forming a CSF circuit that has at least one pump and a catheter. The CSF circuit is configured to channel the flow of the patient's CSF.

In step 620, a therapeutic material is added to the CSF circuit. The therapeutic material (e.g. a drug) may be one or more of methotrexate, a chemotherapy, small interfering RNA (siRNA), microRNA (miRNA), plasmid DNA, messenger RNA (mRNA), small activating RNA (saRNA), splicing-modulatory ASOs, and CRISPR (clustered regularly interspaced short palindromic repeats)/Cas (CRISPR-associated protein, adenoviral vectors (AAV), and an immunosuppressive drug).

In step 630, the patient's CSF is flowed through the CSF circuit using the pump and the catheter at one or more flow rates. The pump may be a dry pump.

In step 640, at least one quality of the CSF is monitored when the CSF is flowing after adding the therapeutic material to the CSF. The at least one quality may include one or more of the following: CSF protein levels; osmolarity; pH levels; glucose levels; CSF pressure; IgG; cytokine levels; sodium levels; potassium levels; or magnesium levels.

In step 650, the one or more flow rates of the CSF are controlled as a function of the monitored qualities of the CSF. The CSF flow rates may be controlled by a flow controller that is configured to increase the rate of flow of the patient's CSF through the CSF circuit to decrease the patient's absorption of the therapeutic material when the concentration of therapeutic material in the CSF is below a threshold concentration. The CSF flow rates may be controlled by a flow controller that is configured to decrease the rate of flow of the patient's CSF through the CSF circuit to increase the patient's absorption of the therapeutic material when the concentration of therapeutic material in the CSF is above a threshold concentration. Furthermore, the flow controller may reverse or stop the flow of the CSF.

One skilled in the art will appreciate further features and advantages of the disclosures based on the provided for descriptions and embodiments. Accordingly, the inventions are not to be limited by what has been particularly shown and described. All publications and references cited herein, including those provided for in Appendix A, are expressly incorporated herein by reference in their entirety.

The embodiments described above are intended to be merely exemplary; numerous variations and modifications will be apparent to those skilled in the art. Such variations and modifications are intended to be within the scope of the present disclosure.

The invention claimed is:

1. A CSF management method for use with a patient having a body with CSF, the method comprising:
   - forming a CSF circuit having at least one pump and catheter, the CSF circuit configured to channel the flow of the patient's CSF;
   - adding a therapeutic material to the CSF circuit;
   - flowing, using the pump and the catheter, the patient's CSF through the CSF circuit at one or more flow rates;
   - monitoring, when CSF is flowing in the CSF circuit, at least one quality of the CSF related to the therapeutic material, the at least one quality including a concentration of the therapeutic material in the CSF, after adding the therapeutic material to the CSF; and
   - controlling the one or more flow rates of the CSF as a function of a monitored concentration of the therapeutic material in the CSF to control absorption or distribution of the therapeutic material.

2. The CSF management method as defined by claim 1, further comprising:
   - determining, as a function of said monitoring, that the concentration of therapeutic material in the CSF is low; further wherein controlling comprises increasing the rate of flow of the patient's CSF through the CSF circuit to decrease the patient's absorption of the therapeutic material.

3. The CSF management method as defined by claim 1, further comprising:
   - determining, as a function of said monitoring, that the concentration of therapeutic material in the CSF is high, further wherein controlling comprises decreasing the rate of flow of the patient's CSF through the CSF circuit to increase the patient's absorption of the therapeutic material.

4. The CSF management method as defined by claim 1, wherein controlling the one or more flow rates comprises reversing the flow of the CSF.

5. The CSF management method as defined by claim 1, further comprising:
   - adding more therapeutic material to the CSF circuit as a function of said monitoring at least one quality of the CSF.

6. The CSF management method as defined by claim 1, wherein the at least one quality comprises one or more of the following: CSF protein levels; osmolarity; pH levels; glucose levels; CSF pressure; IgG; therapeutic material levels; cytokine levels; sodium levels; potassium levels; or magnesium levels.

7. The CSF management method as defined by claim 1, wherein the at least one quality comprises the concentration of a biomarker in the CSF or the concentration of the therapeutic in the CSF.

8. The CSF management method as defined by claim 1, further comprising:
   - disconnecting at least a portion of the CSF circuit to remove control of the flow of the CSF, said disconnecting concluding a single CSF session, said controlling comprising changing the rate of flow of the patient's CSF before said disconnecting.

9. The CSF management method as defined by claim 1, further comprising:
   - disconnecting at least a portion of the CSF circuit to remove control of the flow of the CSF, said disconnecting concluding a single CSF session, said controlling comprising setting a new rate of flow of the patient's CSF after disconnecting, the new rate of flow being used during a later CSF session.

10. The CSF management method as defined by claim 1, wherein said controlling comprises automatically controlling the one or more flow rates of the CSF as a function of the monitored concentration of the therapeutic material in the CSF.

11. The CSF management method as defined by claim 1, further comprising:
   - completing a first CSF session and a second CSF session in series, the method using a first catheter with the first CSF session and a second catheter with the second CSF session, the first catheter and second catheters being different, the first catheter not used during the second CSF session.

12. The CSF management method as defined by claim 1, wherein the CSF circuit has a flow-through segment with at least one sensor configured to monitor the CSF, said monitoring comprising flowing the CSF through the flow-through segment for analysis by the at least one sensor.

13. The CSF management method as defined by claim 1, wherein the CSF circuit comprises an end segment forming an output port, the output port being sealable and configured to enable removal of CSF from the circuit.

14. The CSF management method as defined by claim 13, further comprising:
   - fluidly coupling a removable sample collection container to the output port.

15. The CSF management method as defined by claim 13, wherein the output port comprises a plurality of output ports, the CSF circuit comprising at least one flow controller configured to direct CSF flow toward or away from one or more of the plurality of output ports.

16. The CSF management method as defined by claim 13, further comprising:
   - fluidly coupling a sampler to the output port, the sampler being configured to monitor one or more of the at least one quality of the CSF, further wherein said controlling comprises controlling the one or more flow rates of the CSF after receipt of a sample signal from the sampler, the sample signal having information relating to the concentration of the therapeutic material in the CSF.

17. A CSF management system for use with a patient having a body with CSF and a port to the patient's CSF, the system comprising:
   - a CSF circuit having a catheter and a valve system, the CSF circuit configured to control flow of the patient's CSF and being removably couplable with the patient's port to form a closed fluid flow system, the CSF circuit being accessible via a sealable port;
   - a CSF monitor configured to monitor at least one quality of the CSF related to a therapeutic material, the at least one quality including a concentration of the therapeutic material in the CSF, when the CSF is flowing in the CSF circuit; and
   - a flow controller operatively coupled with the CSF monitor, the flow controller configured to control the flow rate of the CSF through the CSF circuit as a function of a monitored concentration of the therapeutic material in the CSF to control absorption or distribution of the therapeutic material.

18. The CSF management system as defined by claim 17, further comprising:

a pump configured to pump CSF through the CSF circuit, the pump being a dry pump.

19. The CSF management system as defined by claim 17, wherein the flow controller is configured to increase the rate of flow of the patient's CSF through the CSF circuit to decrease the patient's absorption of the therapeutic material when the concentration of therapeutic material in the CSF is below a threshold concentration.

20. The CSF management system as defined by claim 17, wherein the flow controller is configured to decrease the rate of flow of the patient's CSF through the CSF circuit to increase the patient's absorption of the therapeutic material when the concentration of therapeutic material in the CSF is above a threshold concentration.

21. The CSF management system as defined by claim 17, wherein the flow controller is configured to reverse or stop the flow of the CSF.

22. The CSF management system as defined by claim 17, wherein the at least one quality comprises one or more of the following: CSF protein levels; osmolarity; pH levels; glucose levels; CSF pressure; IgG; cytokine levels; sodium levels; potassium levels; or magnesium levels.

23. The CSF management system as defined by claim 17, wherein the at least one quality comprises the concentration of a biomarker in the CSF or the concentration of the therapeutic in the CSF.

24. The CSF management system as defined by claim 17, wherein the flow controller is configured to automatically control the one or more flow rates of the CSF as a function of the concentration of the therapeutic material in the CSF.

25. The CSF management system as defined by claim 17, wherein the CSF circuit has a flow-through segment with at least one sensor configured to monitor the CSF for the at least one quality.

26. The CSF management system as defined by claim 17, wherein the sealable port comprises an end segment forming an output port, the output port being sealable and configured to enable removal of CSF from the circuit.

27. The CSF management system as defined by claim 26, further comprising:

a removable sample collection container that is removably couplable to the output port.

28. The CSF management system as defined by claim 26, wherein the sealable port comprises a plurality of output ports, the flow controller configured to cooperate with the valve system to direct CSF flow toward or away from one or more of the plurality of output ports.

29. The CSF management system as defined by claim 28, further comprising:

a manifold coupled with a plurality of the output ports, the system further comprising a plurality of containers that are removably and sealably couplable with the CSF ports.

30. The CSF management system as defined by claim 17, further comprising:

a sampler configured to fluidly couple with the sealable port, the sampler being configured to monitor one or more of the at least one quality of the CSF, further wherein the flow controller is configured to control the one or more flow rates of the CSF after receipt of a sample signal from the sampler, the sample signal having information relating to the concentration of the therapeutic material in the CSF.

31. The CSF management system as defined by claim 17, wherein said monitoring occurs during a given CSF session and after the given CSF session, further wherein monitoring comprises gathering at least one sample of the CSF for off-site analysis after the end of the CSF session.

32. The CSF management system as defined by claim 17, further comprising a base substrate comprising:

a dry pump and a catheter pump interface for operatively coupling with the catheter;

a manifold having a plurality of output ports configured to receive a plurality of containers for CSF;

at least a portion of the valve system to control fluid flow into the manifold;

a sensor region to receive at least a portion of the CSF monitor;

a guide configured to receive and secure at least a portion of the catheter to the base substrate.

33. The CSF management system as defined by claim 17, wherein the CSF circuit has a flow-through segment with at least one sensor configured to monitor the CSF for the concentration of the therapeutic material in, the CSF management system further comprising a base substrate having:

a dry pump and a catheter pump interface for operatively coupling with the catheter;

a sensor region to receive at least a portion of the CSF monitor;

a guide configured to receive and secure at least a portion of the catheter to the base substrate.

34. A medical kit comprising:

a catheter comprising a body forming a fluid traversing bore, the body having a first end and a second end in fluid communication with the bore, the first and second ends of the body being removably couplable between first and second exterior ports of the patient, the bore being configured to be in fluid communication with both the first and second exterior ports when removably coupled therebetween, the body being configured to form a closed loop CSF channel when removably coupled between the first and second exterior ports, the CSF channel and bore being in fluid communication with the patient's subarachnoid space when the body is removably coupled;

a valve configured to redirect fluid flow within the CSF channel;

a CSF monitor having a sensor configured to monitor at least one quality of the CSF related to the therapeutic material within the closed loop CSF channel; and a flow controller configured to control the flow rate of the CSF through the CSF circuit as a function of a monitored concentration of the therapeutic material in the CSF to control absorption or distribution of the therapeutic material.

35. The medical kit as defined by claim 34, further comprising:

at least one CSF container configured to removably and fluidly couple with the CSF channel.

36. The medical kit as defined by claim 35, further comprising:

a manifold having a plurality of output ports, the manifold being configured to couple with the CSF channel.

37. The medical kit as defined by claim 34, further comprising:

a flow-through segment that is part of the CSF channel, the flow-through segment being part of the catheter or separate from the catheter.

38. The medical kit as defined by claim 34, further comprising:

a therapeutic material reservoir configured to removably couple with the CSF channel.

39. The medical kit as defined by claim 38, wherein the therapeutic material reservoir contains a fluid therapeutic material.

* * * * *